US008846308B2

(12) United States Patent
Greene et al.

(10) Patent No.: US 8,846,308 B2
(45) Date of Patent: Sep. 30, 2014

(54) METHOD FOR IDENTIFYING IMMUNE RESPONSE MODULATORS

(75) Inventors: Mark I. Greene, Penn Valley, PA (US); Bin Li, Chesterbrook, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 840 days.

(21) Appl. No.: 12/663,635

(22) PCT Filed: Jun. 6, 2008

(86) PCT No.: PCT/US2008/066147
§ 371 (c)(1),
(2), (4) Date: Jul. 29, 2010

(87) PCT Pub. No.: WO2008/154399
PCT Pub. Date: Dec. 18, 2008

(65) Prior Publication Data
US 2011/0124560 A1    May 26, 2011

Related U.S. Application Data

(60) Provisional application No. 60/942,764, filed on Jun. 8, 2007.

(51) Int. Cl.
C12Q 1/00        (2006.01)
C12Q 1/68        (2006.01)
C12Q 1/25        (2006.01)
A61K 39/00       (2006.01)
G01N 33/68       (2006.01)

(52) U.S. Cl.
CPC ........ *G01N 33/6872* (2013.01); *G01N 2500/00* (2013.01)
USPC ............. 435/4; 435/6.1; 435/6.13; 424/198.1

(58) Field of Classification Search
None
See application file for complete search history.

(56) References Cited

U.S. PATENT DOCUMENTS

2002/0132300 A1*   9/2002  Hogan et al. ................. 435/69.1
2007/0048394 A1*   3/2007  Yang et al. ..................... 424/764

FOREIGN PATENT DOCUMENTS

WO    WO2008/009977    *  1/2008
WO    WO 2008/154399      12/2008

OTHER PUBLICATIONS

Lopes, J.E., et al. Analysis of FOXP3 reveals multiple domains required for its function as a transcriptional repressor. Journal of Immunology, 2006, vol. 177, p. 3133-3142.*
Schubert, L.A., et al. Scurfin (FOXP3) acts as a repressor of transcription and regulates T cell activation. J. Biol. Chem., 2001, vol. 276, No. 40, p. 37672-37679.*
Li et al., "FOXP3 interactions with histone acetyltransferase and class II histone deacetylases are required for repression" PNAS USA, Mar. 13, 2007, 104(11), 4571-4576.
Li et al., "FOXP3 ensembles in T-cell regulation", Immunol Reviews, Aug. 2006, 212, 99-113.
GenBank Accession No. EF534714, "*Homo sapiens* FOXP3 mRNA, complete cds", May 9, 2007.
GenBank Accession No. CAG33445, "*Homo sapiens* (human) hypothetical protein", Jun. 3, 2004.
GenBank Accession No. AAG47634, "FOXP1 [*Homo sapiens*]", Jan. 11, 2002.
GenBank Accession No. AAG47633, "FOXP1 [*Homo sapiens*]", Jan. 11, 2002.
GenBank Accession No. AAG47632, "FOXP1 [*Homo sapiens*]", Jan. 11, 2002.
GenBank Accession No. AAI31721, "FOXP1 protein [*Homo sapiens*]", Feb. 28, 2007.
GenBank Accession No. AAK69408, "transcription factor FOXP1 [*Homo sapiens*]", Jan. 11, 2002.
GenBank Accession No. BC080521, "*Homo sapiens* forkhead box P1, mRNA (cDNA clone IMAGE:3537750), complete cds", Jul. 15, 2006.
GenBank Accession No. BC071893, "*Homo sapiens* forkhead box P1, mRNA (cDNA clone IMAGE:3537501),complete cds", Jul. 15, 2006.
GenBank Accession No. BC054815, "*Homo sapiens* forkhead box P1, mRNA (cDNA clone IMAGE:5017122), complete cds", Jul. 15, 2006.
GenBank Accession No. BC005055, "*Homo sapiens* forkhead box P1, mRNA (cDNA clone IMAGE:2823199), complete cds", Jul. 15, 2006.
GenBank Accession No. ABQ15210, "FOXP3 [*Homo sapiens*]", May 9, 2007.
GenBank Accession No. AJ006884, "*Homo sapiens* IL-2 promoter and leader sequence", Nov. 14, 2006.
GenBank Accession No. X00695, "Human interleukin-2 (IL-2) gene and 5'-flanking region", Feb. 10, 1999.

* cited by examiner

*Primary Examiner* — Robert Landsman
*Assistant Examiner* — Bruce D Hissong
(74) *Attorney, Agent, or Firm* — Baker & Hostetler LLP

(57) ABSTRACT

Methods of identifying immune response modulators are disclosed. Some methods comprise identifying chemical candidates that modulate oligomerization of FOXP3 and/or fragments thereof comprising the Zinc-LeuZip domains. Some methods comprise identifying chemical candidates that modulate the hetero-oligomerization of FOXP1 with FOXP3 and/or fragments thereof comprising the Zinc-LeuZip domains. Some methods comprise identifying chemical candidates that modulate interaction of IL-2 promoter with FOXP3 and/or fragments thereof comprising the Zinc-LeuZip domains. Method of treating individuals who have or are suspected of having autoimmune disease, inflammatory disease, cell, tissue or organ transplantation, or coronary artery disease, and methods of treating individuals who have or are suspected of having infectious disease, cancer, or who are immunocompromised or undergoing vaccination are disclosed.

1 Claim, 19 Drawing Sheets

C

| IP | IB | 1 | 2 | 3 | 4 | 5 | 6 | 7 | 8 |
|---|---|---|---|---|---|---|---|---|---|
| HA-FOXP3a | | + | - | - | - | + | - | + | - |
| HA-FOXP3a-delE251 | | - | + | - | - | - | + | - | + |
| myc-FOXP3a | | - | - | + | - | + | + | - | - |
| myc-FOXP3a-delE251 | | - | - | - | + | - | - | + | + |
| HA | myc | | | | | ▬ | | | |
| HA | HA | ░ | ▬ | | | ▬ | ▬ | ▬ | ▬ |
| myc | HA | | | | | ▬ | | | |
| myc | myc | | | ▬ | ▬ | ▬ | ▬ | ▬ | ▬ |

D

| IP | IB | 1 | 2 | 3 | 4 |
|---|---|---|---|---|---|
| HA-FOXP3a | | - | + | + | - |
| HA-FOXP3a-delK250 | | - | - | - | + |
| FLAG-FOXP3a | | + | - | + | + |
| HA | FLAG | | | ▬ | |
| HA | HA | | ▬ | ▬ | ▬ |
| FLAG | HA | | | ▬ | |
| FLAG | FLAG | ▬ | | ▬ | ▬ |

FIG. 2

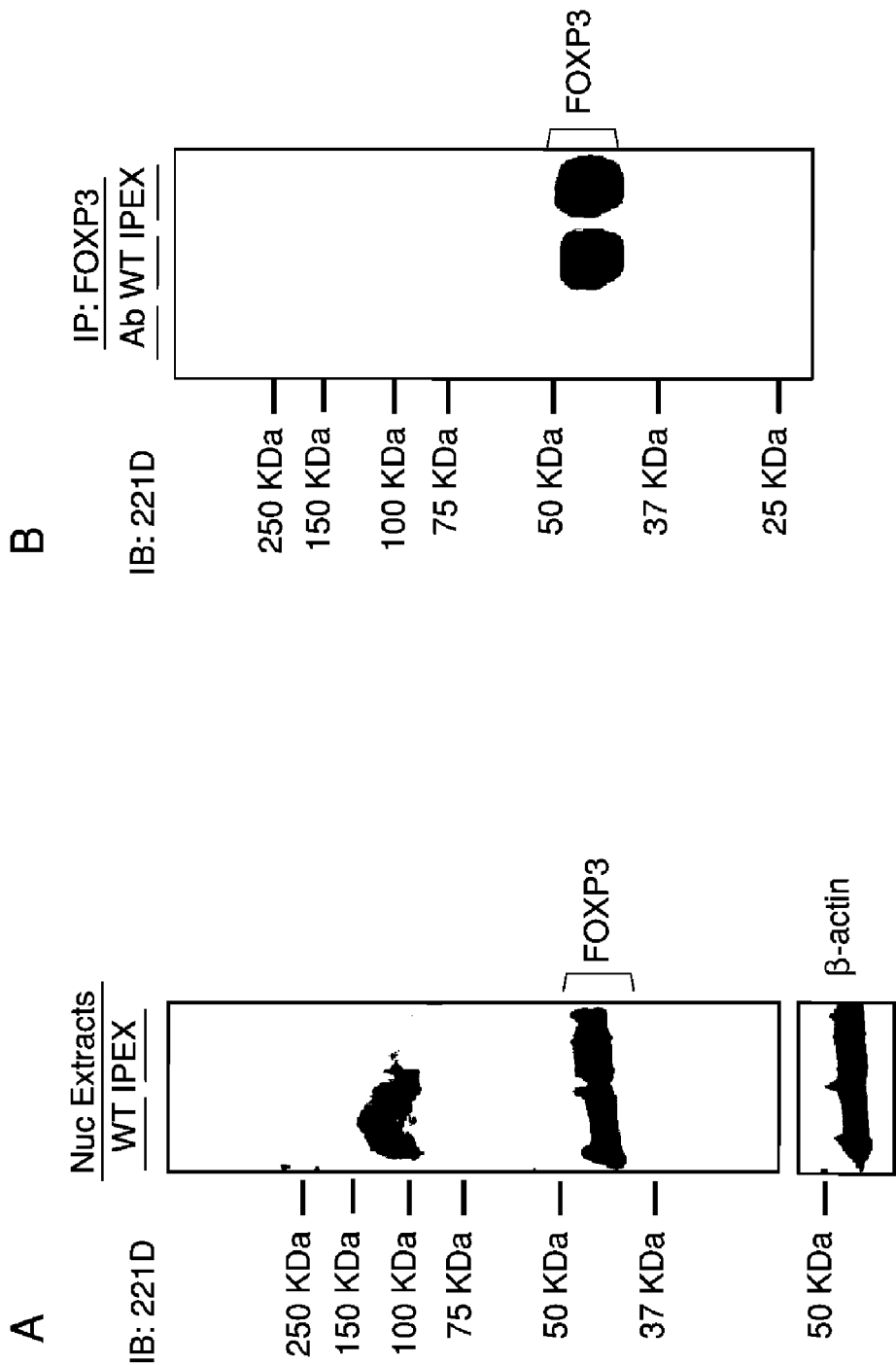

C

D

A

B

SEQUENCE LISTING

```
<160> NUMBER OF SEQ ID NOS: 17

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 1
gacccacctg catgtgaagt c                                              21

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 2
tgggcacgtt gtatttgtct g                                              21

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 3
gagtcatcat ggccaccgac                                                20
```

```
<210> SEQ ID NO 4
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 4
gggatgggag atcaagtggt g                                              21

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 5
tcttgccaag ctggaagact                                                20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 6
atctgatgca tgaagtgtgg                                                20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 7
gacagcaatg gcgagatgag                                                20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 8
cgcagaggcc gactgtttac                                                20

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 9
cgtcgtgatt agcgatgatg                                                20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer
```

```
<400> SEQUENCE: 10
acagagggcc acaatgtgat                                                      20

<210> SEQ ID NO 11
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 11
gctggtgctg gaggagaagc tgagtgcc                                             28

<210> SEQ ID NO 12
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 12
ggcactcagc ttctcctcca gcaccagc                                             28

<210> SEQ ID NO 13
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 13
ctggtgctgg agaagaagct gagtgccatg                                           30

<210> SEQ ID NO 14
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 14
catggcactc agcttcttct ccagcaccag                                           30

<210> SEQ ID NO 15
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 15
ccacaatatg ctattcacat gttcag                                               26

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 16
tggcaggagt tgaggttact g                                                    21

<210> SEQ ID NO 17
```

```
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 17
gaggaaaatt tgtttcatac agaag                                              25
```

METHOD FOR IDENTIFYING IMMUNE RESPONSE MODULATORS

CROSS-REFERENCE TO RELATED APPLICATIONS

This application is the National Stage of International Application No. PCT/US2008/066147, filed Jun. 6, 2008, which claims the benefit of U.S. Provisional Application No. 60/942,764 filed Jun. 8, 2007, the disclosures of which are incorporated herein by reference in their entirety.

BACKGROUND

Maintenance of tolerance to self-antigens is essential for the prevention of autoimmunity that involves regulatory T cells (Treg), but is an incompletely understood process. CD4+CD25+ regulatory T cells have been reported to act as dominant regulators of immune activation and immune tolerance. In humans or in the murine species, one consistent feature of CD4+CD25+ regulatory T cells is the expression of the forkhead family transcription factor FOXP3. FOXP3 acts as a "sufficient" regulator of the development and function of peripheral CD4+CD25+ regulatory T cells, but the molecular mechanisms underlying FOXP3-mediated immunological regulation are still poorly understood.

"X-linked autoimmunity and allergic dysregulation syndrome" (XLAAD) or "Immunodysregulation, polyendocrinopathy and enteropathy, X-linked syndrome" (IPEX) is a fatal recessive disorder of humans that develops in early childhood. These individuals fail to develop CD4$^+$CD25$^+$ T cells and experience varied symptoms that include diarrhea, dermatitis, insulin-dependent diabetes, thyroiditis and anaemia. Massive T cell infiltration into the skin and gastrointestinal tract is also observed. Several XLAAD/IPEX mutations are found in the forkhead domain of FOXP3, indicating the potential disruption of DNA binding. In addition, two independent studies identified single amino acid deletions at E251 or K250 within the leucine zipper domain of FOXP3. Mutations in this region could potentially result in aberrant FOXP3 function by affecting its homo-association or association with the highly conserved leucine zipper domain of other subfamily members, such as FOXP1, FOXP2 and FOXP4.

SUMMARY

The present invention features methods of identifying immune response modulators by measuring various aspects of FOXP3 function.

Certain embodiments relate to methods of identifying an immune response modulator by combining FOXP3 protein, fragments thereof having a Zinc-LeuZip domain, or a mixture of the protein and fragment, with a chemical candidate; measuring oligomer or hetero-oligomer formation of FOXP3 protein or fragments thereof; and comparing the amount of oligomer or hetero-oligomer formation in the presence of the chemical candidate to the amount of oligomer or hetero-oligomer formation in the absence of the chemical candidate, whereby the difference in amount of oligomer or hetero-oligomer formation indicates that the chemical candidate is an immune response modulator. A positive difference in the amount of oligomer or hetero-oligomer formation indicates that the chemical candidate is an immune response inhibitor. A negative difference in the amount of oligomer or hetero-oligomer formation indicates that the chemical candidate is an immune response activator. In certain embodiments the FOXP3 protein or fragments thereof are isolated prior to the combining step. In certain embodiments the combining step occurs in the presence of the chemical candidate.

Certain embodiments relate to methods of identifying an immune response modulator by combining FOXP3 protein or fragments thereof having a Zinc-LeuZip domain and FOXP1 protein with a chemical candidate; measuring hetero-oligomer formation of FOXP3 protein or fragments thereof with FOXP1 protein; and comparing the amount of hetero-oligomer formation in the presence of a chemical candidate to the amount of hetero-oligomer formation in the absence of the chemical candidate, whereby the difference in amount of hetero-oligomer formation indicates that the chemical candidate is an immune response modulator. A positive difference in the amount of hetero-oligomer formation indicates that the chemical candidate is an immune response inhibitor. A negative difference in the amount of hetero-oligomer formation indicates that the chemical candidate is an immune response activator. In certain embodiments the FOXP3 protein or fragments thereof are isolated prior to the combining step. In certain embodiments the combining step occurs in the presence of the chemical candidate.

Certain embodiments relate methods of identifying an immune response modulator by combining FOXP3 protein or fragments thereof having a Zinc-LeuZip domain and a nucleic acid comprising an IL-2 promoter with a chemical candidate; measuring the binding of FOXP3 protein or fragments thereof to the nucleic acid; and comparing the amount of binding of FOXP3 protein or fragments thereof to the nucleic acid in the presence of a chemical candidate to the amount binding of FOXP3 protein or fragments thereof to the nucleic acid in the absence of the chemical candidate, whereby the difference in amount of binding indicates that the chemical candidate is an immune response modulator. A positive difference in the amount of binding indicates that the chemical candidate is an immune response inhibitor. A negative difference in the amount of binding indicates that the chemical candidate is an immune response activator. In certain embodiments the FOXP3 protein or fragments thereof or IL-2 promoter are isolated prior to the combining step. In certain embodiments the combining step occurs in the presence of the chemical candidate. In further embodiments the nucleic acid further comprises a coding region operably linked to the IL-2 promoter.

Certain embodiments relate to methods of identifying an immune response modulator by combining FOXP3 protein or fragments thereof having a Zinc-LeuZip domain and a nucleic acid comprising an IL-2 promoter operably linked to a coding region; measuring transcription of the coding region; and comparing the level of transcription of the coding region that occurs in the presence of a chemical candidate to the level of transcription of the coding region that occurs in the absence of the chemical candidate, whereby the difference in level of transcription indicates that the chemical candidate is an immune response modulator. In further embodiments the combining step includes HDAC7 protein. In further embodiments the combining step includes TIP60 protein. A positive difference in the amount of binding indicates that the chemical candidate is an immune response inhibitor. A negative difference in the amount of binding indicates that the chemical candidate is an immune response activator. In certain embodiments the FOXP3 protein or fragments thereof or HDAC7 protein or TIP60 protein are isolated prior to the combining step. In certain embodiments the combining step occurs in the presence of the chemical candidate.

Certain embodiments relate to methods of treating an individual who has, or is suspected of having, an autoimmune disease, an inflammatory disease, cell, tissue or organ transplantation, or coronary artery disease by identifying an immune response modulator according to any of the other embodiments of the invention, wherein the immune response modulator inhibits the immune response; and administering the immune response modulator to the individual in a therapeutically effective amount. Other embodiments relate to methods of treating an individual who has, or is suspected of having, an infectious disease, cancer, or who is immunocompromised or undergoing vaccination, by identifying an immune response modulator according to any of the other embodiments, wherein the immune response modulator activates the immune response; and administering the immune response modulator to the individual in a therapeutically effective amount.

BRIEF DESCRIPTION OF THE DRAWINGS

FIG. 6A is a schematic of the His6-FOXP3 c-terminal 106-431aa expression construct is depicted for use in bacterial expression and purification.

FIG. 6B is an image of an SDS-PAGE gel wherein the purified His6-FOXP3-c106-431 protein was resolved by gel electophoresis.

FIG. 6C is an image of a developed autoradiographic film detecting binding of FOXP3 wild type and FOXP3 E251 deletion mutant (delE251) to the NFAT sites on the human IL-2 promoter. Nuclear extracts from Jurkat E6.1T cells were transfected with the control empty vector, wild type FOXP3 (WT) expression vector, or delE251 FOXP3 expression vector were used in each binding reaction. Purified His6-FOXP3-C107-431 protein was used as positive control (lane 6). For cold competition, unlabeled double-stranded NFAT probe (lane 5) or unlabeled double-stranded human IL-2 promoter (−374 to +45) (lane 7) in 100-fold molar excess were mixed prior to the addition of labeled probe. For quantification, the autoradiography film was scanned and processed using ImageJ software.

Figure 6:
Figure 6:
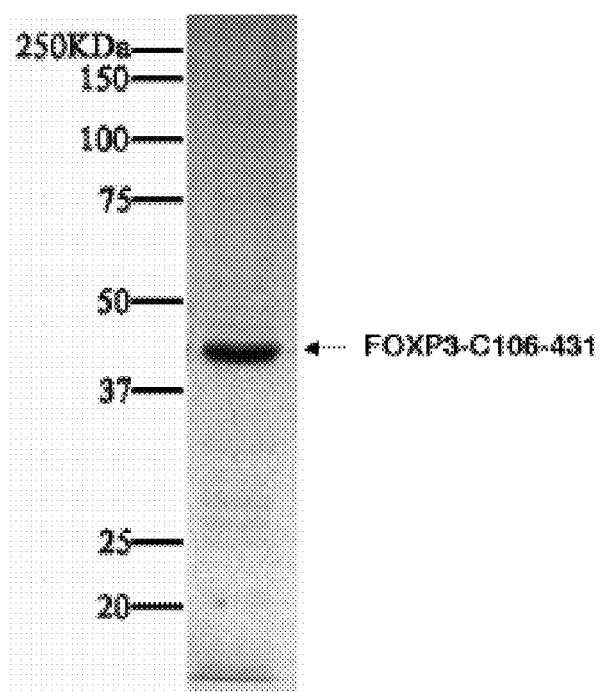
Figure 6:
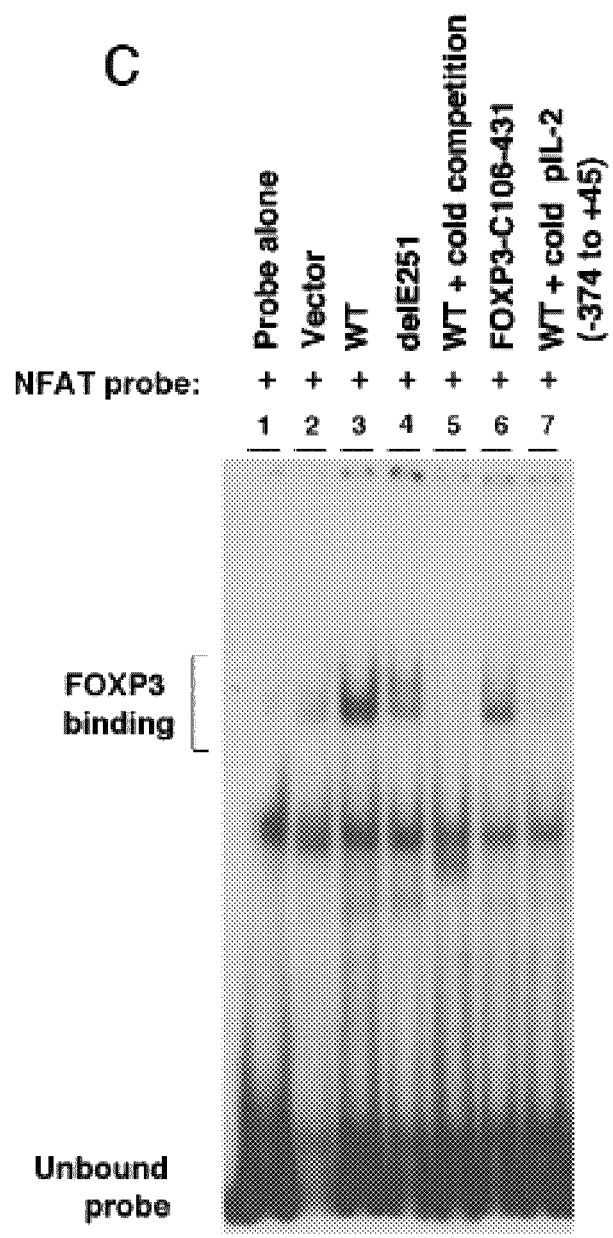
Figure 6D:
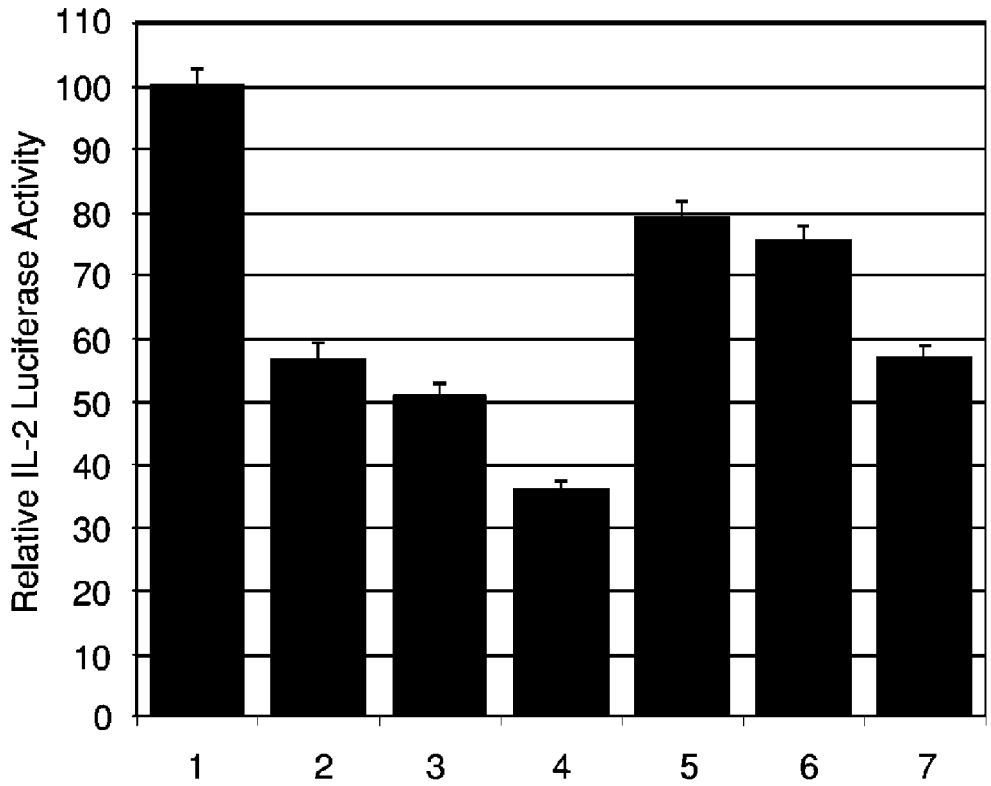

FIG. 6D is a graph of results of an IL-2 promoter luciferase assay of the repression mediated by FOXP3 wild type and FOXP3 delE251 mutant in transfected Jurkat T cells. The results presented are the means of 3 separate experiments with standard deviation. FOXP3 expression levels in cell lysates were analyzed with monoclonal antibody 221D.

Figure 7:
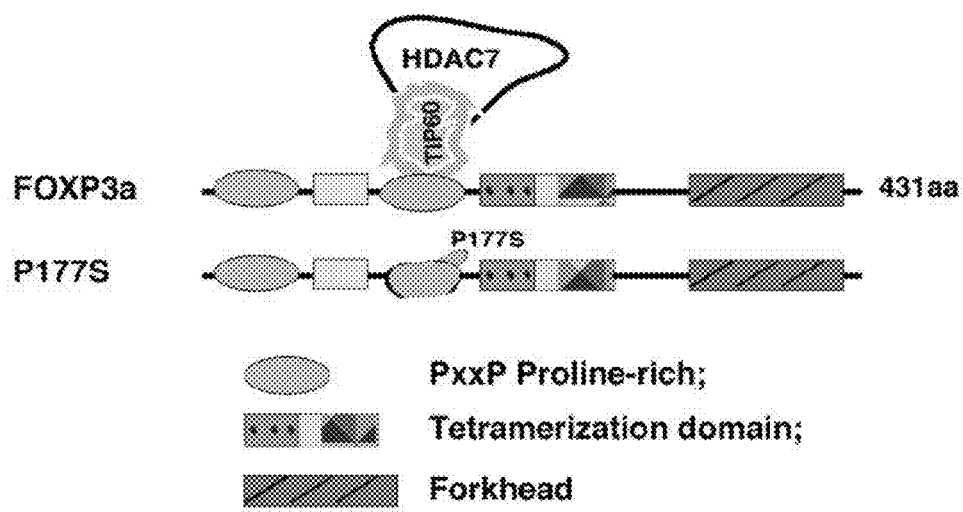
Figure 7:
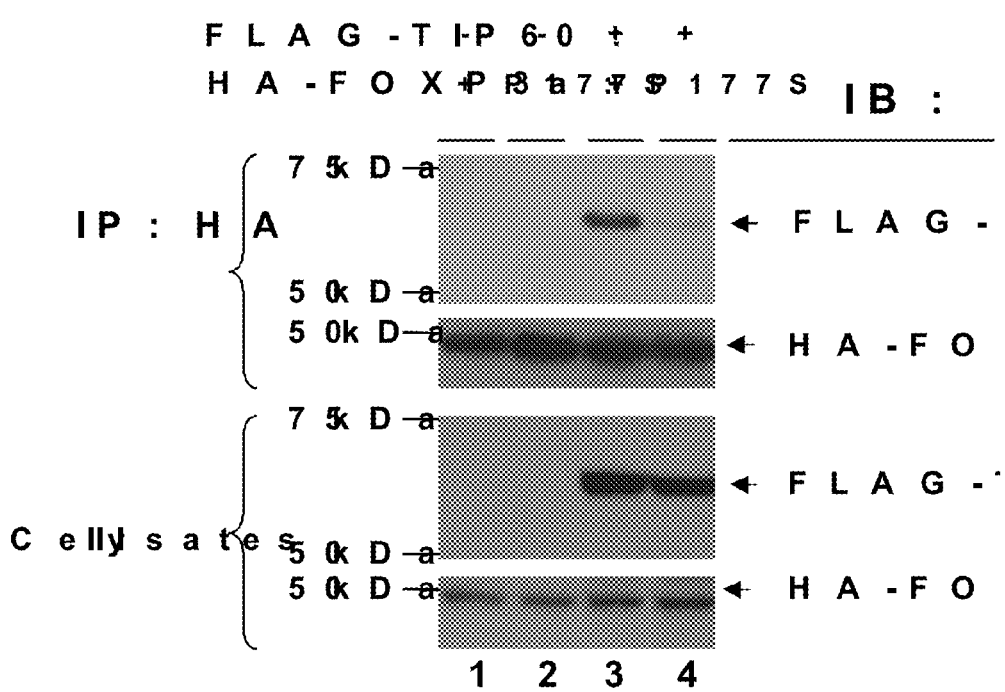

FIG. 7A is a schematic representation of HA tagged FOXP3a and P177S mutant within the proline-rich motif, showing that the PXXP proline-rich motif within the N-terminal 107-190aa of FOXP3 is critical for TIP60 binding.

FIG. 7B is an image of an immunoblot showing that the P177S mutation disrupts FOXP3 association with TIP60 in an immunoprecipitation assay. HEK 293T cells were co-transfected with expression plasmids for FLAG-tagged TIP60, HA-tagged FOXP3a, or HA-tagged P177S. Cells were harvested 48 hours after transfection, immunoprecipitated with anti-HA monoclonal antibody, and subject to immunoblotting with anti-FLAG M2 monoclonal antibody and reprobed with anti-HA-HRP monoclonal antibody. TIP60 and FOXP3 expression levels in cell lysates that were not subject to immunoprecipitation were analyzed by immunoblotting with FLAG M2 and HA-HRP, respectively.

Figure 8:
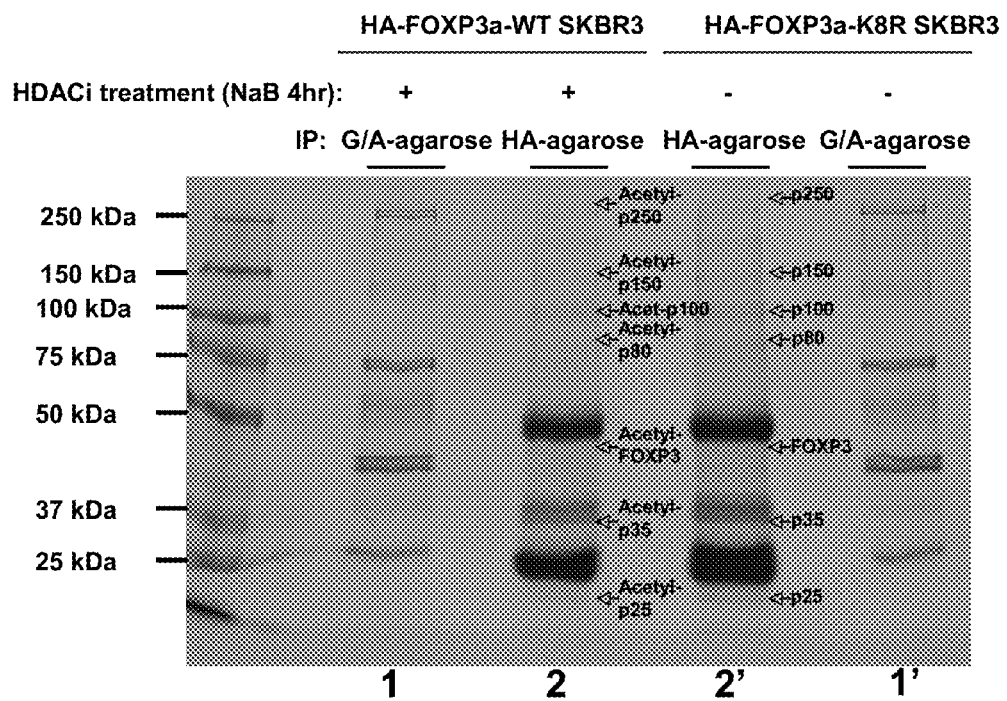

FIG. 8 is an image of an SDS-PAGE electrophoretic gel stained with Silver staining reagent (Invitrogen) showing the FOXP3 repressor complex in FOXP3 stable expressed SKBR3 cells. Nuclear extracts from 100 million wild type HA-FOXP3a or 100 million K8R mutated HA-FOXP3a-K8R expressing SKBR3 cells were grown and a subset of each were treated with histone deacetylase inhibitor. FOXP3a was immunoprecipitated with either protein A/A-agarose or anti-HA-agarose beads, separated by SDS-PAGE, and stained Distinct bands were excised and analyzed with MS/Qstar sequencing.

Figure 9:
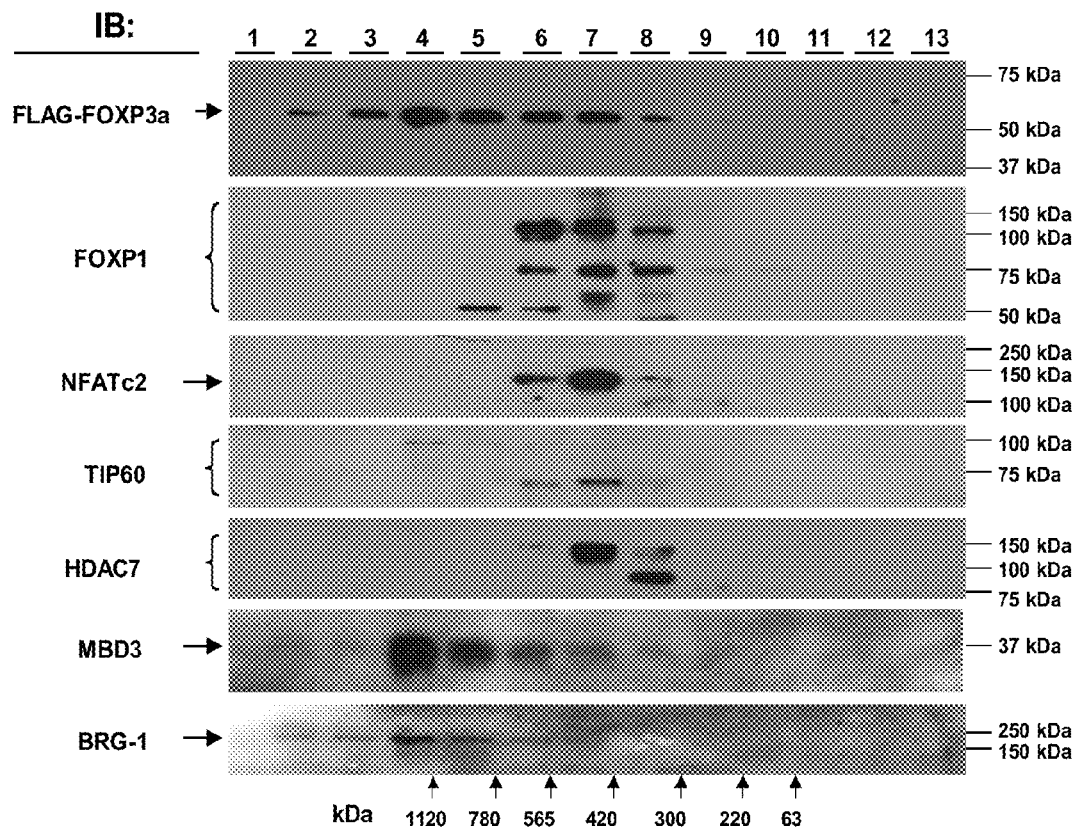

FIG. 9 is an image of an immunoblot showing FOXP3 co-fractionation with transcriptional factors. Following incubation of 400 million FLAG-FOXP3-expressing Jurkat T cells with 50 ng/ml PMA and 1 μM ionomycin for 72 hours, the cell extracts were size-fractionated by gel filtration followed by fraction concentration, resolved by SDS-PAGE gel electrophoresis and subject to immunoblotting with FLAG M2, FOXP1, NFATc2, TIP60, HDAC7, MBD3 or BRG1 antibodies, respectively. TIP60 is observed as a lower MW form in the lower molecular weight FOXP3 complex (FIG. 9 lanes 6, 7, 8). Additionally, a higher MW form of TIP60 was detected in the higher molecular weight FOXP3 complex containing the chromatin remodeling factors (FIG. 9 lanes 4, 5).

Figure 10:
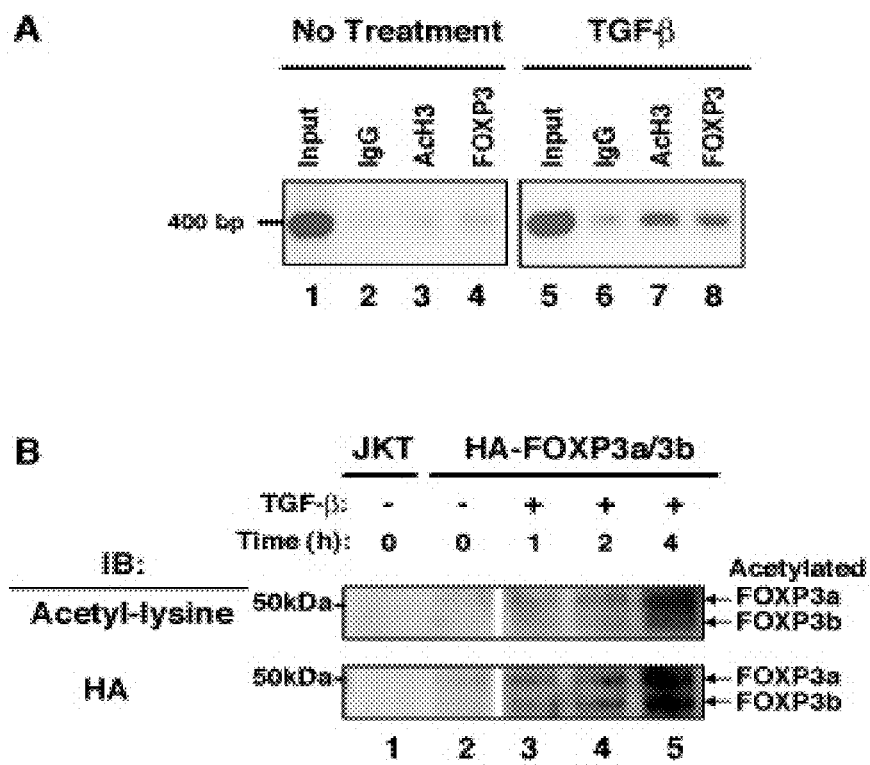

FIG. 10A is an image of an agarose gel resolving PCR amplification products of purified genomic DNA used in a ChIP assay of TGF-β treated and untreated FOXP3 transfected cells. The cell extracts were used for ChIP analysis using mIgG, anti-AcH3, and anti-HA antibodies. Genomic DNA fragments were purified and amplified with hIL-2 promoter specific primers by PCR using Platinum Taq DNA polymerase for 30 amplification cycles. The gel was loaded with 10 μl of PCR amplified material and photographed under UV light.

FIG. 10B is an image of an immunoblot of untreated and TGF-β treated, human HA-FOXP3a/3b transfected Jurkat T cells. The transfected cells were stimulated with or without 1 ng TGF-β per million cells for indicated time periods. Equal amounts of proteins from chromatin rich fractions were separated by SDS-PAGE, transferred to nitrocellulose, and immunoblotted with anti-acetyl lys specific antibody (Ac-K-103, Santa Cruz) followed by reprobing with anti-HA-HRP conjugated antibody. Acetylated FOXP3a and FOXP3b proteins are marked.

DETAILED DESCRIPTION OF ILLUSTRATIVE EMBODIMENTS

FOXP3 Components

As used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

"FOXP3" is a member of the forkhead/winged-helix family of transcriptional regulators and functions as the master regulator in the development and function of regulatory T cells. The amino acid sequence of human FOXP3 is found in Genbank as accession numbers ABQ15210 and NP054728, which are both incorporated herein by reference. The nucleic acid sequence encoding human FOXP3 is found in Genbank as accession number EF534714, which is incorporated herein by reference. FOXP3 comprises at least four known structural motifs or domains that facilitate DNA-protein binding and protein-protein binding. From the N-terminal portion of FOXP3, FOXP3 comprises two proline-rich (PxxP) domains, a zinc-finger domain, a leucine zipper domain, and a forkhead domain (FIG. 2B).

Figure 2:
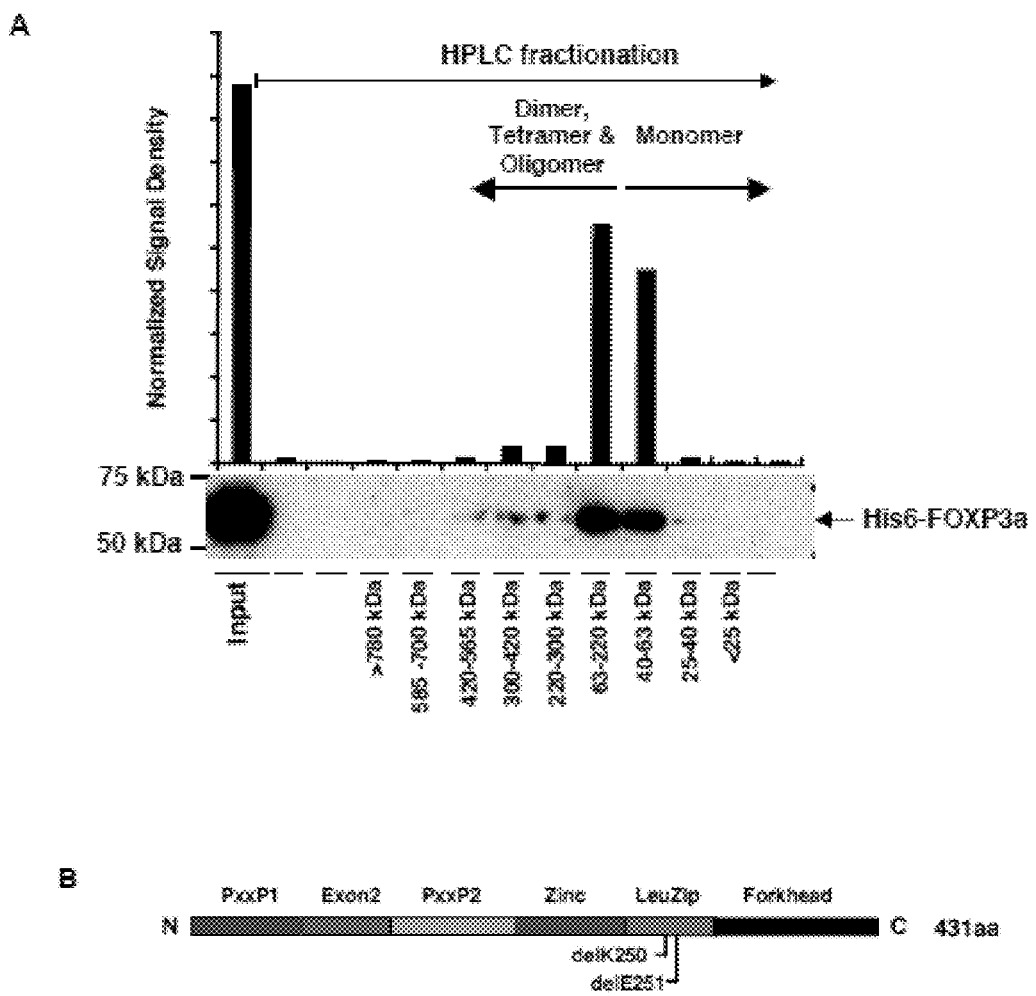
FIG. 2A is an image of an immunoblot and a corresponding graph of the relative amounts of FOXP3a detected by the immunoblot. To generate the immunoblot, purified His-tagged FOXP3a was size fractionated by gel filtration, and the fractions were subject to immunoblotting with anti-FOXP3 antibody. ImageJ software was used for relative quantification of the bands.
FIG. 2B is a schematic representation of FOXP3 subdomains and K250 and E251 deletion mutants (delK250, delE251) within the leucine zipper (LeuZip) domain found in human XLAAD/IPEX syndrome.
FIG. 2C is an image of an immunoblot depicting disruption of a FOXP3 delE251 mutant on homo-association.
FIG. 2D is an image of an immunoblot depicting disruption of a FOXP3 delK250 mutant on homo-association.

The zinc finger-leucine zipper domain ("Zinc-LeuZip domain") of FOXP3 comprises amino acids that reside between the second proline rich domain and the C-terminal forkhead domain (FIG. 2B).

Zinc finger motifs contain cysteine and histidine residues that form a unique three dimensional structure by binding a zinc ion, which facilitates the DNA-binding ability of the protein that contains the motif. Leucine-zipper motifs function using adhesion forces in parallel alpha helices that contain a pattern of leucine residues. This three dimensional structure of Leucine-zipper motifs facilitate the DNA binding ability of the protein that contains the motif.

The FOXP3 gene is mutated in the X-linked syndrome of immunodysregulation, polyendocrinopathy, and enteropathy (IPEX). These mutations were in the forkhead domain of FOXP3. In mice, a FOXP3 mutation (a frameshift mutation that result in protein lacking the forkhead domain) is responsible for "Scurfy," an X-linked recessive mouse mutant that results in lethality in hemizygous males 16 to 25 days after birth. These mice have overproliferation of CD4+ T lymphocytes, extensive multiorgan infiltration, and elevation of numerous cytokines This phenotype is similar to those that lack expression of CTLA-4, TGF-β, human disease IPEX, or deletion of the FOXP3 gene in mice ("scurfy mice"). The pathology observed in scurfy mice seems to result from an inability to properly regulate CD4+ T-cell activity. In mice overexpressing the Foxp3 gene, fewer T cells are observed. The remaining T cells have poor proliferative and cytolytic responses and poor IL2 production, although thymic development appears normal. Histologic analysis indicates that peripheral lymphoid organs, particularly lymph nodes lack cells.

"FOXP1" (also known as "forkhead box P1") is a member of the subfamily P of the forkhead box (FOX) transcription factor family. FOXP1 contains both DNA-binding- and protein-protein binding-domains. This gene may act as a tumor suppressor as it is lost in several tumor types and maps to a chromosomal region (3p14.1) reported to contain a tumor suppressor gene(s). Alternative splicing results in multiple transcript variants encoding different isoforms The amino acid sequence of human FOXP1 is found in Genbank as accession numbers CAG33445, AAG47634, AAG47633, AAG47632, AAI31721 and AAK69408, which are each incorporated herein by reference. The nucleic acid sequence encoding human FOXP3 is found in Genbank as accession numbers BC080521, BC071893, BC054815 and BC005055, which are each incorporated herein by reference.

"Interleukin-2" or "IL-2" is an interleukin, a type of cytokine immune system signaling molecule, that is instrumental in the body's natural response to microbial infection and in discriminating between foreign (non-self) and self. The IL-2 molecule was the first interleukin to be cloned and expressed from a complementary DNA (cDNA) library. IL-2 mediates its effects by binding to IL-2 receptors, which are expressed by lymphocytes, the cells that are responsible for immunity. IL-2 is normally produced by the body during an immune response. When environmental substances gain access to the body, these substances (or antigens) are recognized as foreign by antigen receptors that are expressed on the surface of lymphocytes. Antigen binding to the T cell receptor (TCR) stimulates the secretion of IL-2, and the expression of IL-2 receptors IL-2R. The IL-2/IL-2R interaction then stimulates the growth, differentiation and survival of antigen-selected cytotoxic T cells via the activation of the expression of specific genes. As such, IL-2 is necessary for the development of T cell immunologic memory, one of the unique characteristics of the immune system, which depends upon the expansion of the number and function of antigen-selected T cell clones. IL-2 is also necessary during T cell development in the thymus for the maturation of a unique subset of T cells that are termed regulatory T cells (T-regs).[13][14][15] After exiting from the thymus, T-Regs function to prevent other T cells from recognizing and reacting against "self antigens", which could result in "autoimmunity". T-Regs do so by preventing the responding cells from producing IL-2[14] Thus, IL-2 is required to discriminate between self and non-self, another one of the unique characteristics of the immune system.

"Histone deacetylase 7" or "HDAC7" is an enzyme that removes acetyl groups from an ε-N-acetyl lysine amino acid on a histone. Histones play a role in transcriptional regulation, cell cycle progression, and developmental events. Histone acetylation/deacetylation alters chromosome structure and affects transcription factor access to DNA.

"TIP60" originally identified as cellular HIV-Tat interacting protein and has been shown to augment Tat-dependent transcription. It has also been shown to interact with various cellular transcription factors and to belong to the nuclear histone acetyltransferase (HAT) family. HAT are enzymes that acetylate conserved lysine amino acids on histone proteins by transferring an acetyl group from acetyl CoA to lysine to form ε-N-acetyl lysine. Histone acetylation is generally linked to transcriptional activation.

"Oligomer" refers to compositions having the same mer units. A mer is defined as a unit of an oligomer that originally corresponded to the monomer(s) used in the oligomerization reaction. For example, the mer of a FOXP3 oligomer would be one FOXP3 protein.

"Hetero-oligomer" refers to compositions having the different mer units. A mer is defined as a unit of a hetero-oligomer that originally corresponded to the monomer(s) used in the oligomerization reaction. For example, the mers in a FOXP3-FOXP1 hetero-oligomer would be individual FOXP3 and FOXP1 proteins.

"Oligomerization" or "oligomer formation" refers to the process or reaction that forms oligomers.

"Hetero-oligomerization" or "hetero-oligomer formation" refers to the process or reaction that forms hetero-oligomers.

The terms "polypeptide" or "protein" means molecules having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass components FOXP3 system described herein, or sequences that have deletions from, additions to, and/or substitutions of one or more amino acid of a component of the FOXP3 system.

The term "protein fragment" refers to a protein that has an amino-terminal deletion, a carboxyl-terminal deletion, and/or an internal deletion. In certain embodiments, fragments are at least 5 to about 500 amino acids long. It will be appreciated that in certain embodiments, fragments are at least 5, 6, 8, 10, 15, 20, 30, 40, 50, 60, 70, 80, 90, 100, 110, 150, 200, 250, 300, 350, 400, 450, 500, 1000, 1500, 2000, 2500, or 3000 amino acids long. Particularly useful peptide fragments include functional domains, including binding domains.

"Transcription" refers to the synthesis of RNA under the direction of DNA. DNA sequence is enzymatically copied by RNA polymerase to produce a complementary nucleotide RNA strand, called messenger RNA (mRNA), because it carries a genetic message from the DNA to the protein-synthesizing machinery of the cell. One significant difference between RNA and DNA sequence is the presence of U, or uracil in RNA instead of the T, or thymine of DNA. In the case of protein-encoding DNA, transcription is the first step that usually leads to the expression of the genes, by the production of the mRNA intermediate, which is a faithful transcript of the gene's protein-building instruction. Skilled artisans are familiar with methods to measure transcription including increases or decreases in transcription.

"Promoter" is a regulatory region of DNA generally located upstream (towards the 5' region of the sense strand) of a gene that generally promotes transcription of the gene. The promoter contains specific DNA sequences, response elements, that are recognized by proteins known as transcription factors. These factors bind to the promoter sequences, recruiting RNA polymerase, the enzyme that synthesizes the RNA from the coding region of the gene. As promoters are typically immediately adjacent to the gene in question, positions in the promoter are designated relative to the transcriptional start site, where transcription of RNA begins for a particular gene (i.e., positions upstream are negative numbers counting back from −1, for example −100 is a position 100 base pairs upstream). Many eukaryotic promoters, but not all, contain a TATA box (sequence TATAAA), which in turn binds a TATA binding protein which assists in the formation of the RNA polymerase transcriptional complex. The TATA box typically lies very close to the transcriptional start site (often within 50 bases). Eukaryotic promoter regulatory sequences typically bind proteins called transcription factors which are involved in the formation of the transcriptional complex. An example is the E-box (sequence CACGTG), which binds transcription factors in the basic-helix-loop-helix (bHLH) family (e.g. BMAL1-Clock, cMyc).

"Coding region" refers to the region of a gene is the portion of DNA or RNA that is transcribed into another RNA, such as a messenger RNA or a non-coding RNA (for instance a transfer RNA or a ribosomal RNA). A transcript can then be translated into proteins. This does not include gene regions such as a recognition site, initiator sequence, or termination sequence, only the region that will directly code for amino acid linkage.

Using standard techniques and readily available starting materials, a nucleic acid molecule that encodes FOXP3 protein or FOXP1 protein may be isolated from a cDNA library, using probes which are designed using the nucleotide sequence information disclosed in the Genbank sequences disclosed herein. A cDNA library may be generated by well known techniques. One having ordinary skill in the art can isolate a nucleic acid molecule that encodes FOXP3 protein or FOXP1 protein, and insert it into an expression vector using standard techniques and readily available starting materials.

As used herein, the term "recombinant expression vector" is meant to refer to a plasmid, phage, viral particle or other vector which, when introduced into an appropriate host, contains the necessary genetic elements to direct expression of the coding sequence that encodes the FOXP3 protein, or fragments thereof comprising the Zinc-LeuZip domains, or FOXP1 protein. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. The recombinant expression vectors are useful for transforming hosts to prepare recombinant expression systems for preparing FOXP3 protein, or fragments thereof comprising the Zinc-LeuZip domains, or FOXP1 protein.

A host cell that comprises the recombinant expression vector that comprises a nucleotide sequence that encodes FOXP3 protein, or fragments thereof comprising the Zinc-LeuZip domains, or FOXP1 protein can be used to produce FOXP3 protein, or fragments thereof comprising the Zinc-LeuZip domains, or FOXP1 protein. Host cells for use in well known recombinant expression systems for production of proteins are well known and readily available. Examples of host cells include bacteria cells such as *E. coli*, yeast cells such as *S. cerevisiae*, insect cells such as *S. frugiptera*, non-human mammalian tissue culture cells Chinese hamster ovary (CHO) cells and human tissue culture cells such as HeLa cells.

In some embodiments, for example, one having ordinary skill in the art can, using well known techniques, insert such DNA molecules into a commercially available expression vector for use in well known expression systems. For example, the commercially available plasmid pSE420 (Invitrogen, San Diego, Calif.) may be used for production of collagen in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I (Invitrogen, San Diego, Calif.) may, for example, be used for production in mammalian cells such as Chinese Hamster Ovary cells. One having ordinary skill in the art can use these commercial expression vectors and systems or others to produce FOXP3 protein, or fragments thereof comprising the Zinc-LeuZip domains, or FOXP1 protein thereof using routine techniques and readily available starting materials. (See e.g., Sambrook et al., Molecular Cloning a Laboratory Manual, Second Ed. Cold Spring Harbor Press (1989) which is incorporated herein by reference.) Thus, the desired proteins can be prepared in both prokaryotic and eukaryotic systems, resulting in a spectrum of processed forms of the protein. One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., Molecular Cloning a Laboratory Manual, Second Ed. Cold Spring Harbor Press (1989).

The most commonly used prokaryotic system remains *E. coli*, although other systems such as *B. subtilis* and *Pseudomonas* are also useful. Suitable control sequences for prokaryotic systems include both constitutive and inducible promoters including the lac promoter, the trp promoter, hybrid promoters such as tac promoter, the lambda phage P1 promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion. A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein.

Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth. Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, e.g. the baculovirus polyhedron promoter. As above, promoters can be either constitutive or inducible. For example, in mammalian systems, the mouse metallothionein promoter can be induced by the addition of heavy metal ions.

The particulars for the construction of expression systems suitable for desired hosts are known to those in the art. Briefly, for recombinant production of the protein, the DNA encoding the polypeptide is suitably ligated into the expression vector of choice. The DNA is operably linked to all regulatory elements which are necessary for expression of the DNA in the selected host. One having ordinary skill in the art can, using well known techniques, prepare expression vectors for recombinant production of the polypeptide. The expression vector including the DNA that encodes FOXP3 protein, or fragments thereof comprising the Zinc-LeuZip LeuZip domains, or FOXP1 protein is used to transform the compatible host which is then cultured and maintained under conditions wherein expression of the foreign DNA takes place Modulators of FOXP3 Activity The term "modulator" means a compound which can increase ("activate") or decrease ("inhibit") FOXP3 oligomerization, hetero-oligomerization, binding to DNA, and/or transcriptional repressive activity. The term "chemical candidate" refers to any molecule, e.g. proteins (which herein includes proteins, polypeptides, and peptides), small organic or inorganic molecules, polysaccharides, polynucleotides, etc. which are to be tested for FOXP3 oligomerization, hetero-oligomerization, binding to DNA, and/or transcriptional repressive activity. Chemical candidates encompass numerous chemical classes. In a preferred embodiment, the chemical candidates are organic molecules, particularly small organic molecules, comprising functional groups necessary for structural interaction with proteins, particularly hydrogen bonding, and typically include at least an amine, carbonyl, hydroxyl or carboxyl group, preferably at least two of the functional chemical groups. The chemical candidates often comprise cyclical carbon or heterocyclic structures and/or aromatic or polyaromatic structures substituted with one or more chemical functional groups.

Chemical candidates are obtained from a wide variety of sources, as will be appreciated by those in the art, including libraries of synthetic or natural compounds. As will be appreciated by those in the art, embodiments of the invention provide a method for screening any library of chemical candidates, including the wide variety of known combinatorial chemistry-type libraries.

In certain aspects, chemical candidates are synthetic compounds. A number of techniques are available for the random and directed synthesis of a wide variety of organic compounds and biomolecules, including expression of randomized oligonucleotides. Alternatively, other aspects use libraries of natural compounds in the form of bacterial, fungal, plant and animal extracts that are available or readily produced. Moreover, natural or synthetically produced libraries and compounds are readily modified through conventional chemical, physical and biochemical means. Known pharmacological agents may be subjected to directed or random chemical modifications, including enzymatic modifications, to produce structural analogs.

Where the chemical candidates are proteins, they may be naturally occurring proteins or fragments of naturally occurring proteins. Thus, for example, cellular extracts containing proteins, or random or directed digests of proteinaceous cellular extracts, may be tested. In this way libraries of prokaryotic and eukaryotic proteins may be made for screening against any number of compositions. Particularly preferred in this embodiment are libraries of bacterial, fungal, viral, and mammalian proteins, with the latter being preferred, and human proteins being especially preferred.

In other aspects, the chemical candidates are peptides ranging in size from about 2 to about 50 amino acids, with from about 5 to about 30 amino acids being preferred, and from about 8 to about 20 being particularly preferred. The peptides may be digests of naturally occurring proteins as is outlined above, random peptides, or "biased" random peptides. The term "randomized" is intended to mean that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

Where the embodiment uses a library, the library should provide a sufficiently structurally diverse population of randomized agents to effect a probabilistically sufficient range of diversity to allow interaction with a particular FOXP3 component. Accordingly, an interaction library must be large enough so that at least one of its members will have a structure that interacts with a FOXP3 component. Those skilled in the art would understand how to best construct a sufficiently large and diverse library.

Further embodiments relate to a fully randomized library, with no sequence preferences or constants at any position. In other aspects, the library is biased, wherein some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In some aspects, the chemical candidates are nucleic acids. With reference to chemical candidates, "nucleic acid" or "oligonucleotide" used herein means at least two nucleotides covalently linked together. Embodiments composed of nucleic acids will generally contain phosphodiester bonds, although in some cases, as outlined below, nucleic acid analogs are included that may have alternate backbones, comprising, for example, phosphoramide, phosphorothioate, phosphorodithioate, O-methylphophoroamidite linkages, and peptide nucleic acid backbones and linkages. Other analog nucleic acids include those with positive backbones; non-ionic backbones, and non-ribose backbones. Nucleic acids containing one or more carbocyclic sugars are also included within the definition of nucleic acids. These modifications of the ribose-phosphate backbone may be done to facilitate the addition of additional moieties such as labels, or to increase the stability and half-life of such molecules in physiological environments. As will be appreciated by those in the art, all of these nucleic acid analogs may find use in various inventive embodiments. In addition, mixtures of naturally occurring nucleic acids and analogs can be made. Alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids.

Further embodiments include chemical candidates that are organic molecules or chemicals with organic moieties, wherein the molecule or moiety can be synthesized from a series of substrates that can be chemically modified. "Chemically modified" includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the candidates to form new substrates or agents which can then be tested in various embodiments.

As will be appreciated by those in the art, it is possible to screen more than one type of chemical candidates at a time. Thus, the library of chemical candidates used may include only one type of agent (i.e. peptides), or multiple types (peptides and organic agents). The assay of several chemical candidates at one time is further discussed below.

FOXP3 Assays

Certain embodiments provide methods of combining the FOXP3 components, which include FOXP3 or fragments thereof as well as other entities with which FOXP3 or fragments thereof interact. By "combining" is meant the addition of the various components into a receptacle under conditions whereby FOXP3 oligomerization, hetero-oligomerization, binding to DNA, and/or transcriptional repression take place. In a preferred embodiment, the receptacle is a single tube. Other embodiments include a well of a 96-well plate or other commercially available multi-well plate. In an alternative embodiment, the receptacle is the reaction vessel of a FACS machine. Other receptacles include, but are not limited to 384 well plates and 1536 well plates. Still other suitable receptacles will be apparent to the skilled artisan.

The addition of the assay FOXP3 components may be sequential or in a predetermined order or grouping, as long as the conditions amenable to FOXP3 activity are obtained. Such conditions are well known in the art, and further guidance is provided below.

The FOXP3 components are combined under reaction conditions that oligomerization, hetero-oligomerization, binding to DNA, and/or transcriptional repression take place. Generally, this will be physiological conditions. Incubations may be performed at any temperature which facilitates optimal activity, typically between about 4 and 40° C. Incubation periods are selected for optimum activity, but may also be optimized to facilitate rapid high through put screening.

A variety of other reagents may be included in the assay. These include reagents like salts, solvents, buffers, neutral proteins, e.g. albumin, detergents, etc. which may be used to facilitate optimal oligomerization, hetero-oligomerization, DNA-protein binding, transcriptional repression and/or reduce non-specific or background interactions. Also reagents that otherwise improve the efficiency of the assay, such as protease inhibitors, nuclease inhibitors, anti-microbial agents, etc., may be used.

The mixture of FOXP3 components may be added in any order that promotes oligomerization, hetero-oligomerization, binding to DNA, and/or transcriptional repression or optimizes identification of a modulator's effect. In a preferred embodiment, the FOXP3 components are provided in a reaction buffer solution, followed by addition of the chemical candidate.

In a preferred embodiment, a tag is attached to a FOXP3 component. In a preferred embodiment, the tag attached to the FOXP3 component is an enzyme label or a binding pair member which is indirectly labeled with an enzyme label. In this latter preferred embodiment, the enzyme label substrate produces a fluorescent reaction product. For instance, the binding of a FOXP3 component may be measured by luminescence. Equipment for such measurement is commercially available and easily used by one of ordinary skill in the art to make such a measurement.

Other modes of measuring a bound FOXP3 component are well known in the art and easily identified by the skilled artisan for each of the labels described herein. For instance, radioisotope labeling may be measured by scintillation counting, or by densitometry after exposure to a photographic emulsion, or by using a device such as a Phosphorimager.

In preferred embodiments, the FOXP3 component is bound to a solid support. This may be done directly or by using a linker or tag, such as His, GST, and the like, that is attached to a FOXP3 component (or fragment thereof), wherein the adapter is a surface substrate binding molecule.

Other aspects relate to a FOXP3 component that is bound, directly or via a substrate binding element, to a bead. Following ligation, the beads may be separated from the unbound FOXP3 component and the bound FOXP3 component measured. In a preferred embodiment, FOXP3 component is bound to beads and the composition used includes tag wherein tag is a fluorescent label. In this embodiment, the beads with bound FOXP3 component may be separated using a fluorescence-activated cell sorting (FACS) machine. The amount of bound FOXP3 component can then be measured.

In a preferred embodiment, multiple assays are performed simultaneously in a high throughput screening system. In this embodiment, multiple assays may be performed in multiple receptacles, such as the wells of a 96 well plate or other multi-well plate. As will be appreciated by one of skill in the art, such a system may be applied to the assay of multiple chemical candidates and/or and/or multiple combinations of FOXP3 components. In a preferred embodiment, a high-throughput screening system may be used for determining the FOXP3 oligomerization, hetero-oligomerization, binding to DNA, and/or transcriptional repression with different chemical candidate combinations. Other features relate to a high throughput screening system for simultaneously testing the effect of individual chemical candidates.

It is understood by the skilled artisan that the steps of the assays provided herein can vary in order. It is also understood, however, that while various options (of chemical candidates, properties selected or order of steps) are provided herein, the options are also each provided individually, and can each be individually segregated from the other options provided herein. Moreover, steps which are obvious and known in the art that will increase the sensitivity of the assay are intended to be within the scope of this invention. For example, there may be additionally washing steps, blocking steps, etc.

Methods of Detecting FOXP3 Activity

FOXP3 components may be detected via the use of antibodies. Anti-FOXP3 antibodies are available from Santa Cruz Biotechnology, Santa Cruz, Calif., Catalog Numbers: sc-56680, sc-53876, sc-52899, sc-28705, sc-31739, sc-21072 and sc-31738. Anti-FOXP3 antibodies are available from eBioscience, San Diego, Calif. Catalog Numbers 14-4776, 13-4776, 11-4776, 71-5776, 12-4776, 72-5776, 15-4776, 17-4776, 77-5776, 53-4776, 73-5776, 51-4776, 56-4776, 57-4776, 00-5523, 88-8999, 88-8998, 88-8995, 88-4999, 88-4994, 14-4777, 13-4777, 11-4777, 12-4777, 72-5774, 17-4777, 77-5774, 53-4777, 73-5774, 51-4777, 57-4777 and 00-5523. Anti-FOXP3 antibodies are available from ABCAM, Cambridge UK, Catalog Number: ab10563. Anti-FOXP1 antibodies are available from Santa Cruz Biotechnology, Santa Cruz, Calif., Catalog Number: sc-31731. Anti- FOXP1 antibodies are available from ABCAM, Cambridge UK, Catalog Number: ab16645.

Antibodies which specifically bind to FOXP3 protein or FOXP1 protein may be used to purify the respective protein from natural sources using well known techniques and readily available starting materials. Such antibodies may also be used to purify FOXP3 protein or FOXP1 protein from material present when producing FOXP3 protein or FOXP1 protein by recombinant DNA methodology.

The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) ANTIBODIES: A Laboratory Manual, Cold Spring Harbor Laboratory, Cold Spring Harbor, N.Y. which is incorporated herein by reference. Briefly for example, full length FOXP3 protein or FOXP1 protein, or an immunogenic fragment thereof is injected into mice. The spleen of the mouse is removed; the spleen cells are isolated and fused with immortalized mouse cells. The hybrid cells, or hybridomas, are cultured and those cells which secrete antibodies are selected. The antibodies are analyzed and, if found to specifically bind to the FOXP3 protein or FOXP1 protein, the hybridoma which produces them is cultured to produce a continuous supply of antibodies. The antibody can then be tested to determine if it inhibits FOXP3 oligomerization, hetero-oligomerization, DNA binding, and/or transcriptional repression In further embodiments, one or more components of the assay comprise a tag. By "tag" is meant an attached molecule or molecules useful for the identification or isolation of the attached component. Components having a tag are referred to as "tag-X", wherein X is the component. For example, a FOXP3 component comprising a tag is referred to herein as "tag-FOXP3" or "tag-FOXP1," or whatever the case may be. Preferably, the tag is covalently bound to the attached component. When more than one component of a combination has a tag, the tags will be numbered for identification, for example "tag1-FOXP3." Preferred tags include, but are not limited to, a label, a partner of a binding pair, and a surface substrate binding molecule. As will be evident to the skilled artisan, many molecules may find use as more than one type of tag, depending upon how the tag is used.

By "label" is meant a molecule that can be directly (i.e., a primary label) or indirectly (i.e., a secondary label) detected; for example a label can be visualized and/or measured or otherwise identified so that its presence or absence can be known. As will be appreciated by those in the art, the manner in which this is done will depend on the label. Preferred labels include, but are not limited to, fluorescent labels, label enzymes, and radioisotopes.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malachite green, stilbene, Lucifer Yellow, Cascade Blue™, and Texas Red. Suitable optical dyes are described in the 1996 Molecular Probes Handbook by Richard P. Haugland, hereby expressly incorporated by reference. Suitable fluorescent labels also include, but are not limited to, green fluorescent protein (GFP), blue fluorescent protein (BFP), enhanced yellow fluorescent protein (EYFP), luciferase, β-galactosidase, and Renilla.

By "label enzyme" is meant an enzyme which may be reacted in the presence of a label enzyme substrate which produces a detectable product. Suitable label enzymes include but are not limited to, horseradish peroxidase, alkaline phosphatase and glucose oxidase. Methods for the use of such substrates are well known in the art. The presence of the label enzyme is generally revealed through the enzyme's catalysis of a reaction with a label enzyme substrate, producing an identifiable product. Such products may be opaque, such as the reaction of horseradish peroxidase with tetramethyl benzedine, and may have a variety of colors. Other label enzyme substrates, such as Luminol, have been developed that produce fluorescent reaction products. Methods for identifying label enzymes with label enzyme substrates are well known in the art and many commercial kits are available.

By "radioisotope" is meant any radioactive molecule. Suitable radioisotopes include, but are not limited to $^{14}$C, $^{3}$H, $^{32}$P, $^{33}$P, $^{35}$S, $^{125}$I, and $^{131}$I. The use of radioisotopes as labels is well known in the art.

In addition, labels may be indirectly detected, that is, the tag is a partner of a binding pair. By "partner of a binding pair" is meant one of a first and a second moiety, wherein said first and said second moiety have a specific binding affinity for each other. Suitable binding pairs include, but are not limited to, antigens/antibodies (for example, digoxigenin/anti-digoxigenin, dinitrophenyl (DNP)/anti-DNP, dansyl-X-anti-dansyl, Fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Other suitable binding pairs include polypeptides such as FLAG; the KT3 epitope peptide; tubulin epitope peptide; and the T7 gene 10 protein peptide tag, and the antibodies each thereto. Generally, in a preferred embodiment, the smaller of the binding pair partners serves as the tag, as steric considerations in FOXP3 component oligomerization may be important. As will be appreciated by those in the art, binding pair partners may be used in applications other than for labeling, as is further described below.

As will be appreciated by those in the art, a partner of one binding pair may also be a partner of another binding pair. For example, an antigen (first moiety) may bind to a first antibody (second moiety) which may, in turn, be an antigen to a second antibody (third moiety). It will be further appreciated that such a circumstance allows indirect binding of a first moiety and a third moiety via an intermediary second moiety that is a binding pair partner to each.

As will be appreciated by those in the art, a partner of a binding pair may comprise a label, as described above. It will further be appreciated that this allows for a tag to be indirectly labeled upon the binding of a binding partner comprising a label. Attaching a label to a tag which is a partner of a binding pair, as just described, is referred to herein as "indirect labeling".

As will be appreciated by those in the art, tag-components can be made in various ways, depending largely upon the form of the tag. Components and tags are preferably attached by a covalent bond. The production of tag-polypeptides by recombinant means when the tag is also a polypeptide is described below.

Biotinylation of target molecules and substrates is well known, for example, a large number of biotinylation agents are known, including amine-reactive and thiol-reactive agents, for the biotinylation of proteins, nucleic acids, carbohydrates, carboxylic acids. A biotinylated substrate can be attached to a biotinylated component via avidin or streptavidin. Similarly, a large number of haptenylation reagents are also known.

Methods for labeling of proteins with radioisotopes are known in the art.

Production of proteins having His-tags by recombinant means is well known, and kits for producing such proteins are commercially available.

The functionalization of labels with chemically reactive groups such as thiols, amines, carboxyls, etc. is generally known in the art. In a preferred embodiment, the tag is functionalized to facilitate covalent attachment.

The covalent attachment of the tag may be either direct or via a linker. In one embodiment, the linker is a relatively short coupling moiety, that is used to attach the molecules. A coupling moiety may be synthesized directly onto a FOXP3 component, FOXP3 for example, and contains at least one functional group to facilitate attachment of the tag. Alternatively, the coupling moiety may have at least two functional groups, which are used to attach a functionalized component to a functionalized tag, for example. In an additional embodiment, the linker is a polymer. In this embodiment, covalent attachment is accomplished either directly, or through the use of coupling moieties from the component or tag to the polymer. In a preferred embodiment, the covalent attachment is direct, that is, no linker is used. In this embodiment, the component preferably contains a functional group such as a carboxylic acid which is used for direct attachment to the functionalized tag. It should be understood that the component and tag may be attached in a variety of ways, including those listed above. What is important is that manner of attachment does not significantly alter the functionality of the component. For example, in tag-FOXP3, the tag should be attached in such a manner as to allow the FOXP3 to be covalently bound to other FOXP3. As will be appreciated by those in the art, the above description of covalent attachment of a label and FOXP3 applies equally to the attachment of virtually any two molecules of the present disclosure.

In certain embodiments, the tag is functionalized to facilitate covalent attachment, as is generally outlined above. Thus, a wide variety of tags are commercially available which contain functional groups, including, but not limited to, isothiocyanate groups, amino groups, haloacetyl groups, maleimides, succinimidyl esters, and sulfonyl halides, all of which may be used to covalently attach the tag to a second molecule, as is described herein. The choice of the functional group of the tag will depend on the site of attachment to either a linker, as outlined above. Thus, for example, for direct linkage to a carboxylic acid group of a ubiquitin, amino modified or hydrazine modified tags will be used for coupling via carbodiimide chemistry, for example using 1-ethyl-3-(3-dimethylaminopropyl)-carbodiimide (EDAC) as is known in the art. In one embodiment, the carbodiimide is first attached to the tag, such as is commercially available for many of the tags described herein.

Further embodiments involve using cloned and expressed components (including fragments) of the FOXP3 components. The processes involved in cloning and expression, such as polymerase chain reactions, expression vectors, cellular transfection and transformation, are well known in the art.

FOXP3 components may also be made as a fusion protein, using techniques well known in the art. Thus, for example, the protein may be made as a fusion protein to increase expression, or for other reasons. For example, when the protein is a peptide, the nucleic acid encoding the peptide may be linked to other nucleic acid for expression purposes. Similarly, FOXP3 components may be linked to protein labels, such as green fluorescent protein (GFP), red fluorescent protein (RFP), blue fluorescent protein (BFP), yellow fluorescent protein (YFP), etc.

In addition the other methods described above, one skilled in the art would recognize that other detection methods would also be suitable in various embodiments, such as fluoresence polarization, fluorescence resonance transfer, or chromogenicity.

The various FOXP3 components may be used in various embodiments in "isolated" form. "Isolated protein" referred to herein means that a subject protein (1) is free of at least some other proteins with which it would normally be found, (2) is essentially free of other proteins from the same source, e.g., from the same species, (3) is expressed by a cell from the same species or a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of synthetic origin, or any combination thereof. Preferably, the isolated protein is substantially free from proteins or polypeptides or other contaminants that are found in its natural environment that would interfere with its use (therapeutic, diagnostic, prophylactic, research or otherwise).

Proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, FOXP3 protein may be purified using a standard anti-FOXP3 antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the protein. In some instances no purification will be necessary.

One having ordinary skill in the art can, using well known techniques, isolate FOXP3 protein, or fragments thereof comprising the Zinc-LeuZip domains, or FOXP1 protein that is produced using such expression systems. The methods of purifying FOXP3 protein, or fragments thereof comprising the Zinc-LeuZip domains, or FOXP1 protein from natural sources using antibodies which specifically bind to FOXP3 protein, or fragments thereof comprising the Zinc-LeuZip domains, or FOXP1 protein as described above, may be equally applied to purifying FOXP3 protein, or fragments thereof comprising the Zinc-LeuZip domains, or FOXP1 protein produced by recombinant DNA methodology Uses of Immune Response Modulators Chemical candidates that are identified as inhibiting homo-oligomerization of FOXP3 and/or fragments thereof comprising the Zinc-LeuZip domains, or inhibiting hetero-oligomerization of FOXP3 and/or fragments thereof comprising the Zinc-LeuZip domains with FOXP1, or inhibiting FOXP3 and/or fragments thereof comprising the Zinc-LeuZip domains binding to IL-2 promoter may be useful as vaccine adjuvants, in the treatment of infectious diseases, in the treatment of immunocompromised individuals, and in the treatment of cancer. Examples of vaccines include protein subunit vaccines, recombinant vaccines, killed or attenuated vaccines, and DNA vaccines. One or more chemical candidates identified according to methods described herein may be administered to individuals in an amount of effective to impart a therapeutic benefit including increasing immune responses against antigens.

Chemical candidates that are identified as inhibiting homo-oligomerization of FOXP3 and/or fragments thereof comprising the Zinc-LeuZip domains, or inhibiting hetero-oligomerization of FOXP3 and/or fragments thereof comprising the Zinc-LeuZip domains with FOXP1, or inhibiting FOXP3 and/or fragments thereof comprising the Zinc-LeuZip domains, binding to IL-2 promoter may be further tested using other in vitro or in vivo protocols. Alternatively, compounds identified using other in vitro or in vivo protocols as having potential as vaccine adjuvants or for activity against infectious diseases, or in other applications involving immunostimulants may be tested to determine if they inhibit homo-oligomerization of FOXP3 and/or fragments thereof comprising the Zinc-LeuZip domains, inhibit hetero-oligomerization of FOXP3 and/or fragments thereof comprising the Zinc-LeuZip domains with FOXP1, or inhibit FOXP3 and/or fragments thereof comprising the Zinc-LeuZip domains, binding to IL-2 promoter.

Chemical candidates that are identified as enhancing homo-oligomerization of FOXP3 and/or fragments thereof comprising the Zinc-LeuZip domains, or enhancing hetero-oligomerization of FOXP3 and/or fragments thereof comprising the Zinc-LeuZip domains with FOXP1, or enhancing FOXP3 and/or fragments thereof comprising the Zinc-LeuZip domains binding to IL-2 promoter may be useful in the treatment of autoimmune and inflammatory diseases, in the treatment of transplantation patients, and in the treatment of coronary artery disease, and in other applications involving immunosuppressants. Examples of autoimmune diseases include T cell mediated autoimmune diseases such as Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Other examples of autoimmune diseases include B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Examples of conditions associated with transplantation include rejection of cell, tissue or organ transplants and graft versus host disease. Examples of inflammatory diseases include sepsis, SIRS, septic shock, and toxic shock. Such conditions and diseases may be treated by administered to individuals who have such conditions and diseases, an amount of one or more chemical candidate identified according to methods described herein effective to impart a therapeutic benefit including relief or reduction in severity of symptoms, or otherwise a detectable amelioration or reduction in disease.

Chemical candidates that are identified as enhancing homo-oligomerization of FOXP3 and/or fragments thereof comprising the Zinc-LeuZip domains, or enhancing hetero-oligomerization of FOXP3 and/or fragments thereof comprising the Zinc-LeuZip domains with FOXP1, or enhancing FOXP3 and/or fragments thereof comprising the Zinc-LeuZip domains binding to IL-2 promoter may be further tested using other in vitro or in vivo protocols. Alternatively, chemical candidates identified using other in vitro or in vivo protocols as having potential for activity against autoimmune and inflammatory diseases, or for the treatment of transplantation patients, or for the treatment of coronary artery disease, or in other applications involving immunosuppressants may be tested to determine if they enhance homo-oligomerization of FOXP3 and/or fragments thereof comprising the Zinc-LeuZip domains, or enhance hetero-oligomerization of FOXP3 and/or fragments thereof comprising the Zinc-LeuZip domains with FOXP1, or enhance FOXP3 and/or fragments thereof comprising the Zinc-LeuZip domains, binding to IL-2 promoter.

The following examples serve to more fully describe the manner of using the above-described invention. It is understood that these examples in no way serve to limit the true scope of this invention, but rather are presented for illustrative purposes. All references cited herein are expressly incorporated by reference in their entirety.

EXAMPLES

Example 1

General Methods

Cell Lines

Human IPEX patient T cell lines containing the E251 deletion mutation of FOXP3 (delE251), and control lines expressing wild type FOXP3 have been described in the art. These are primary PHA plus IL-2 driven T cell lines. The cells were mixed with irradiated (2500 rad) PBMC feeders (1:2 ratio) derived from normal hosts. PHA and IL-2 (1-10 µg PHA-P and 100 units/ml IL-2) were added to the culture, cells were then split after 3 days and expanded with IL-2 alone. The expansion phase lasted for 10-14 days with fresh IL-2 supplemented media added every 2-4 days. The feeder cycle was repeated until necessary cell numbers were achieved.

RNA Isolation and RT-PCR

Total RNA was isolated from 2 million FACStar sorted mouse $CD4^+CD25^+$ or $CD4^+CD25^-$ cells with Agilent Total RNA Isolation Mini Kit (Part No. 5185-6000, Agilent Technologies, CA), and reverse-transcribed with StrataScript™ First-strand synthesis kit (Cat. #200420, Stratagene, CA). Transcription of Foxp1, Foxp2, FOXP3, Foxp4 was measured by nonsaturating PCR using the following primers: Foxp1 5'-GACCCACCTGCATGTGAAGTC-3' (SEQ ID NO:1), and 5'-TGGGCACGTTGTATTTGTCTG-3' (SEQ ID NO:2), Foxp2 5'-GAGTCATCATGGCCACCGAC-3' (SEQ ID NO:3), and 5'-GGGATGGGAGATCAAGTGGTG-3' (SEQ ID NO:4), FOXP3 5'-TCTTGCCAAGCTGGAAGACT-3' (SEQ ID NO:5), and 5'-ATCTGATGCATGAAGTGTGG-3' (SEQ ID NO:6), Foxp4 5'-GACAGCAATGGCGAGAT-GAG-3' (SEQ ID NO:7), and 5'-CGCAGAGGCCGACT-GTTTAC-3' (SEQ ID NO:8). The housekeeping gene hprt (hypoxanthine-guanine phosphoribosyl-transferase) primers 5'-CGTCGTGATTAGCGATGATG-3' (SEQ ID NO:9), and 5'-ACAGAGGGCCACAATGTGAT-3' (SEQ ID NO:10), were used as an endogenous reference.

Human $CD4^+CD25^+$ T Cells

Human $FOXP3^+CD4^+CD25^+$ T cells were obtained by in vitro expansion as follows: two hundred million PBLs were stained for CD4 and CD25, and using a Mo Flo high speed sorter, the brightest (top 1%) $CD4^+CD25^+$ cells were purified. These cells were stimulated with anti-CD3, anti-CD28 coated beads using a 3 bead to 1 cell ratio in the presence of high levels of IL-2 (300 U/ml) and cultured in RPMI with 10%

FCS for the next 20-25 days. These in vitro expanded regulatory T cells from CD25$^{high}$CD4$^+$ subpopulation remain functional, as indicated by their ability to mediate suppressive activity in in vitro assays. Additionally, they maintain a high level of FOXP3 expression compared with in vitro expanded CD25$^-$CD4$^+$ T cells.

Protein Purification and Molecular Weight Determination

The Zinc-LeuZip (190-263) encoding region of both wild type FOXP3 and the E251 deletion mutant of FOXP3 were amplified by PCR, digested and subcloned into pET-21a-MBP to obtain MBP-Zinc-LeuZip(MBP-WT) and MBP-delE251-Zinc-LeuZip(MBP-delE251) expressing constructs. MBP fusion proteins or MBP alone were highly expressed in BL21, and purified by amylose affinity chromatography. The determination of protein molecular weights in solution was based on the elution volume from a Superdex 200 gel filtration column. Gel Filtration HMW and LMW Calibration Kits (Amersham Biosciences) were used for the calibration of Superdex 200 gel filtration column (Protein KW-803).

The nucleic acid sequence encoding the c-terminal 106-431aa of FOXP3 (FOXP3-c106-431) was subcloned to pET28-a (Novagen). Protein was expressed in E. coli BL21 (DE3) carrying one chaperone plasmid pG-Tf2 (Takara), bound to Ni-NTA resin (Qiagen) equilibrated with buffer A (50 mM NaH2PO4, pH 7.5, 300 mM NaCl, 1 mM DTT, 0.1% Tween-20), eluted with 100-200 mM imidazole in buffer A, then further purified by Superdex-200 column (Amersham Biosciences) equilibrated in buffer B (50 mM NaH2PO4, pH 7.5, 200 mM NaCl, 1 mM DTT).

Nuclear extract size fractionation Nuclear extracts of human CD4$^+$CD25$^+$ T cells were quantified with the BCA™ Protein Assay Kit (Pierce), and applied to a calibrated GFC column Protein KW-803 (Shodex®, Japan) run by a HPLC apparatus (Waters Corporation, USA) with the nuclear extraction buffer as the HPLC running buffer. One column volume (18.84 ml) was collected in 1.0 ml aliquots. Equal volumes of collected fractions were subjected to 8% SDS-PAGE and immunoblotting with indicated antibodies.

Plasmids and Antibodies

The following antibodies were used: anti-FOXP3 mAb hFOXY and PCH101 from eBioscience; anti-myc (9E10), HA (F-7), BRG-1 (H-88), NFATc2 (4G6-G5), from Santa Cruz Biotechnology; anti-FLAG-M2 from Sigma; anti-MEF2D from BD Biosciences Pharmingen; anti-FOXP3 221D/D3; anti-FOXP1 JC12; FOXP1 expression construct was a kind gift of Dr. Edward Morrisey, Univ. of Pennsylvania. FOXP3a (the large isoform) and FOXP3b (the small isoform lacking exon 2) have been described previously.

Site-Directed Mutagenesis of FOXP3 delE251 and delK250

The following primers were used to make FOXP3 delK250 and delE251 mutants respectively: 5'-GCT GGT GCT GGA GGA GAA GCT GAG TGC C-3' (SEQ ID NO:11) and 5'-GGC ACT CAG CTT CTC CTC CAG CAC CAG C-3' (SEQ ID NO:12); 5'-CTG GTG CTG GAG AAG AAG CTG AGT GCC ATG-3' (SEQ ID NO:13) and 5'-CAT GGC ACT CAG CTT CTT CTC CAG CAC CAG-3' (SEQ ID NO:14). All the mutants were made with QuickChange™ site-directed mutagenesis kit (Stratagene) and confirmed by DNA sequencing.

ShRNA Vectors and Reagent

TRC shRNA (Lenti) targeting human FOXP1 construct TRCN0000015664 (sh64) and the Arrest-In transfection reagent (cat no. ATR1741) were purchased from Open Biosystem. The non-target shRNA control vector was purchased from Sigma (cat no. SHC002).

Chromatin Cross-Linking and Immunoprecipitation (ChIP) Assay

A human IPEX patient T cell line expressing the E251 FOXP3 mutation and the normal control line expressing a similar amount of wild type FOXP3 were expanded in vitro. CHIP Analyses were performed with the EZ Chip™ Chromatin Immunoprecipitation Kit (Cat#17-371, Upstate). ChIP antibodies included: mouse IgG (#15381, Sigma), anti-FOXP3 (hFOXY #14-5779, eBioscience), and anti-acetylated histone H4 (#17-229, Upstate). PCR primers for human IL-2 primers are as follows: hIL-2F-374: 5'-CCACAATAT-GCTATTCACATGTTCAG-3' (SEQ ID NO:15) and hIL-2R-45: 5'-TGGCAGGAGTTGAGGTTACTG-3' (SEQ ID NO:16).

Electrophoretic Mobility Shift Assay (EMSA)

Nuclear extracts were prepared and EMSA assay were performed as previously described. The oligonucleotide probe used corresponded to the NFAT binding site with consensus sequence: 5'-GAGGAAAATTTGTTTCATACA-GAAG-3' (SEQ ID NO:17). In each binding reaction 10 µg of protein from nuclear extracts and 100,000 cpm labeled probe were used per 20 µl of binding reaction. The binding buffer composition was 20 mM Hepes, pH 7.9, 50 mM KCl, 5 mM MgCl2, 3 mM DTT, 0.1 mg BSA, 0.25 mg/ml poly dI/dC and 10% glycerol. For cold competition, a 100-fold molar excess of unlabeled double stranded probe was mixed prior to the addition of labeled probe.

Dual Luciferase Assay

Jurkat transient transfections and all luciferase assays were performed as previously described. The transfected Jurkat T cells were stimulated with 50 ng/ml of PMA and 1 µM ionomycin for 6-7 hours before lysing cells and analyzed by means of dual luciferase assay normalized with Renilla luciferase activity according to the manufacturer's protocol (Promega).

Example 2

FOXP3 Oligomer Formation

Figures 1A, 1B:
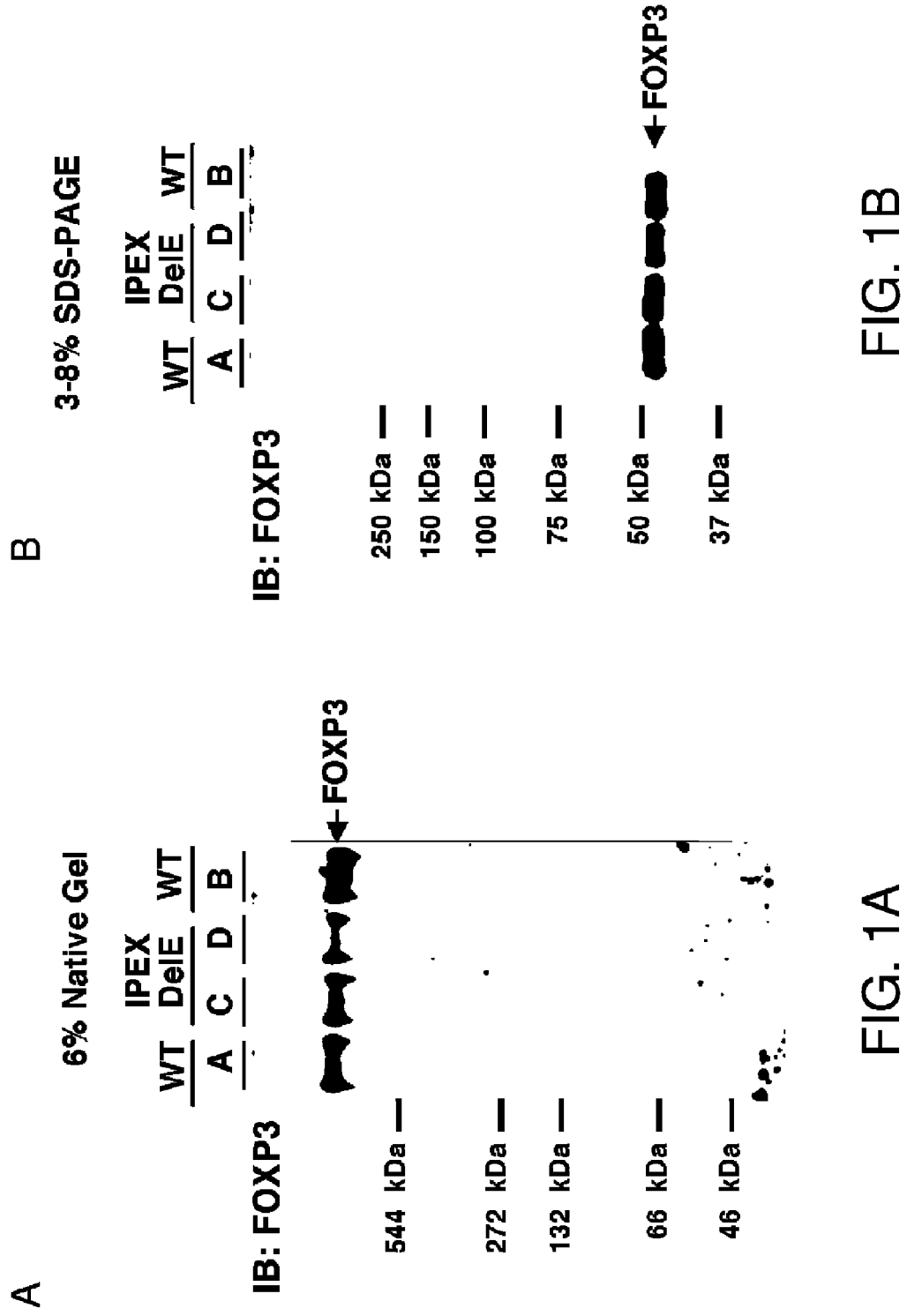
FIG. 1A is an image of an immunoblot wherein 20 μg of nuclear extracts were resolved on a 6% native gel electrophoresis followed by immunoblotting with anti-human FOXP3 monoclonal antibody 221D. Samples A and B are from human T cell lines with wild type FOXP3, while C and D are from XLAAD/IPEX patient T cells with FOXP3 delE251 mutations. A protein molecular weight marker kit for non-denaturing polyacrylamide gel electrophoresis (Sigma) was used to determine the protein molecular weight on a native gel.
FIG. 1B is an image of an immunoblot, wherein 20 μg of nuclear extracts were resolved on 3-8% denaturing SDS-PAGE electophoresis followed by immunoblotting with anti-human FOXP3 monoclonal antibody 221D, using the same samples described under FIG. 1A, above.

FOXP3 derived from cells of patients with the rare genetic disease, X-linked autoimmunity-allergic dysregulation syndrome (XLAAD), where FOXP3 is dysfunctional, was studied. Using this model system certain subdomains of FOXP3 that are functionally important were identified. Nuclear extracts from two human primary T cell lines, A and B, expressing wild type FOXP3 and two XLAAD/IPEX patient T cell lines, C and D, which express a mutated FOXP3 gene with a single amino acid deletion at E251 were isolated. Under native conditions, both the endogenous wild type FOXP3 and its delE251 mutant assembled as part of a large protein complex with a molecular weight higher than 500 kDa, although it appears that there are slightly reduced amounts of endogenous delE251 mutant protein associated within the large complex (FIG. 1A). Under reducing conditions, both wild type FOXP3 and its delE251 mutant migrate as a monomer with a molecular weight around 47 kDa (FIG. 1B).

Nuclear extracts from Flag tagged delE251 FOXP3a (the large isoform) ectopically transfected Jurkat T cells were fractionated by size with an HPLC gel filtration column, followed by SDS-PAGE and western blotting analysis with anti-FLAG M2 mAb. Using this approach, the endogenous ~47 kDa delE251 FOXP3a protein still resided principally in two separated high molecular weight (MW) complexes, one with MW over 696 kDa (FIG. 1C lane 4), and the other with MW between 696 kDa and 354 kDa (FIG. 1C lane 7 and 8).

Figure 1C:
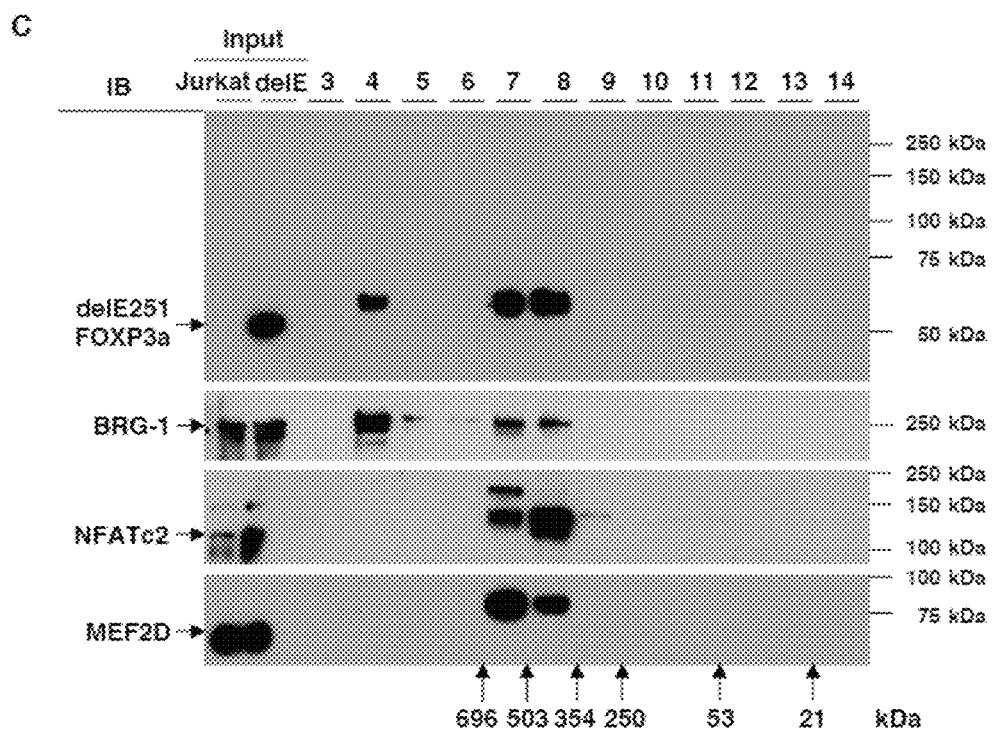
FIG. 1C is an image of an immunoblot wherein nuclear extracts of FLAG-delE251 FOXP3a expressing Jurkat T cells were size fractionated by gel filtration followed by fraction concentration, resolution by denaturing SDS-PAGE gel electrophoresis, and immunoblotting with anti-FLAG, anti-BRG-1, or anti-MEF2D.

BRG-1, a catalytic subunit of mammalian chromatin-remodeling complexes, which found in association with FOXP3 by MS/Qstar spectrometric analysis after co-immunoprecipitation, cofractionates with both FOXP3 ensemble complexes (FIG. 1C lanes 4, and lane 7, 8). One previously described FOXP3 associated transcriptional factor NFATc2; as well as another transcription factor, MEF2D, known to associate with HDAC7, were found to co-fractionate with the lower molecular weight FOXP3 complex, with MW between 354 kDa and 696 kDa (FIG. 1C lane 7, 8). Both are absent from the higher MW fractions of FOXP3 associated proteins (FIG. 1C lane 4). Accordingly, FOXP3 exists in a dynamic supramolecular complex. HDAC7, TIP60 and the NFATc2 and MEF2D transcription factors may be present in certain fractions.

Example 3

Zinc Finger and Leucine Zipper Domains Mediate FOXP3 Oligomerization

Full length FOXP3a (the large isoform) with a 6× His tag was expressed in Sf9 insect cells and purified by Ni-NTA column. The purified His-tagged full length FOXP3a was size fractionated, followed by SDS-PAGE and immunoblotting of the individual fractions with anti-FOXP3 mAb 221D. Purified full length FOXP3a eluted from the gel filtration column as a dominant mixture of monomers, dimers, tetramers, and a detectable amount of oligomeric species (FIG. 2A).

Analysis of the FOXP3 protein revealed a conserved C2H2 zinc finger and one leucine zipper motif (FIG. 2B), which mediated DNA binding as well as function in homo- and hetero-oligomerization, a process that has already been demonstrated for other FOXP subfamily members. FOXP3 may exists as monomeric, dimeric, tetrameric, and even higher oligomeric species with the dimeric or tetrameric associations determined by the combined zinc finger and leucine zipper domains.

Full-length FOXP3 E251 and K250 deletion mutants were created by site-directed mutagenesis and subcloned into mammalian expression vectors containing either myc or HA epitope tags at the N-terminus. HEK293T cells were transfected with the myc-tagged wild type FOXP3, myc-tagged FOXP3-delE251, HA-tagged wild type FOXP3, or HA-tagged FOXP3-delE251 vectors as indicated (FIG. 2C). The HA-tagged wild type FOXP3 species was able to homo-associate with the myc-tagged wild type FOXP3, but not with the myc-tagged delE251 mutant, and vice versa (FIG. 2C). Similar experiments were performed with FOXP3 K250 deletion mutant constructs and it was found that the FOXP3 delK250 mutant also could not homo-associate (FIG. 2D). Thus the leucine zipper domain is essential for FOXP3 homo-association.

Figure 3:
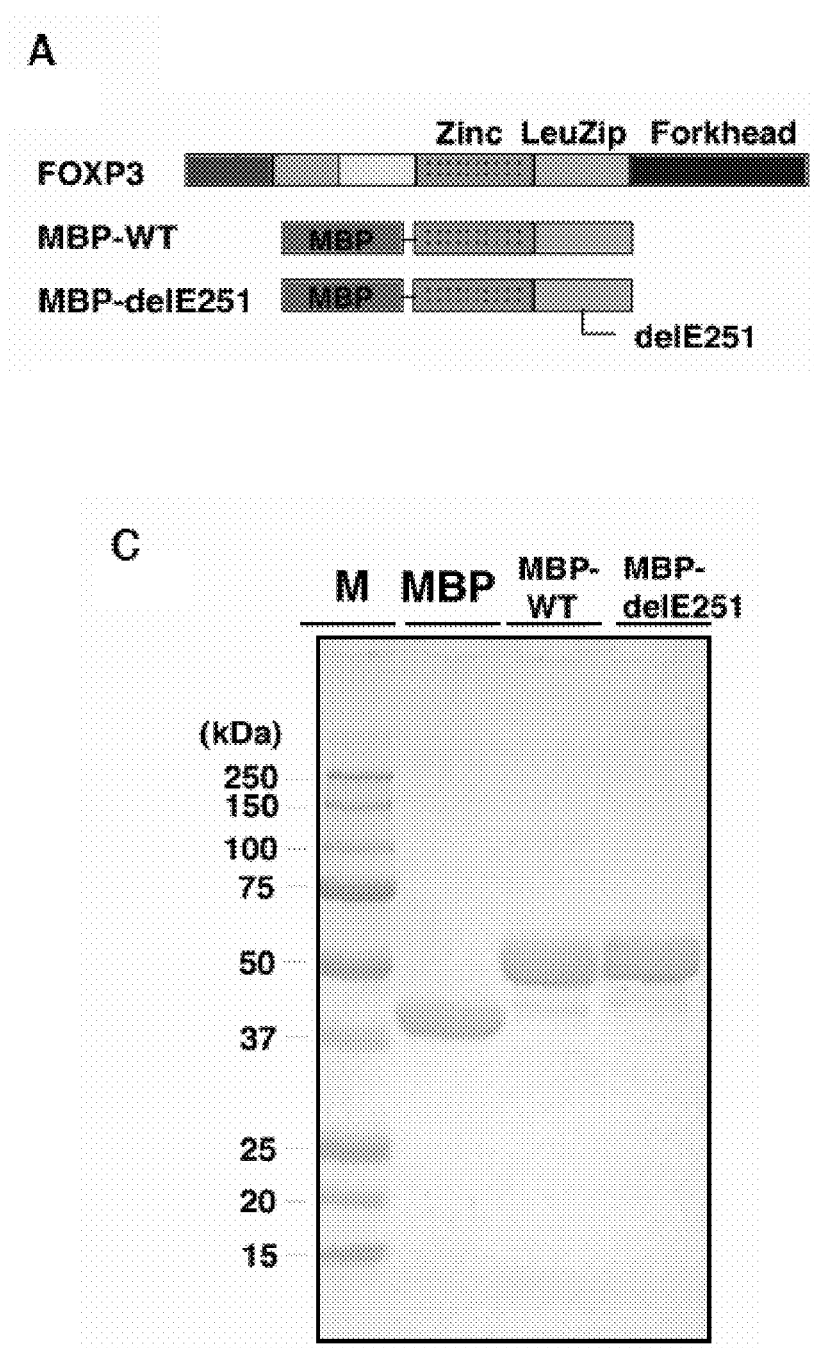
FIG. 3A is a schematic representation of FOXP3 subdomains and the wild type and delE251 mutated MBP-Zinc-LeuZip constructs, which shows, among other things, that the delE251 construct contains a deletion.
FIG. 3B is a chromatograph of the purified MBP fusion proteins by Superdex 200 chromatography, wherein both wild type and delE251 MBP-Zinc-LeuZip eluted as a single peak with a calculated molecular weight of 225 kDa and 58.8 kDa, respectively, and MBP alone eluted as a single peak with a molecular weight of 43.5 kDa.
FIG. 3C is an image of an SDS-PAGE gel wherein purified FOXP3 MBP-WT and MBP-delE251 Zinc-LeuZip proteins were resolved by denaturing gel electrophoresis under reducing conditions using 100 mM DTT), revealing that the proteins migrate as a monomer.
Figure 3:
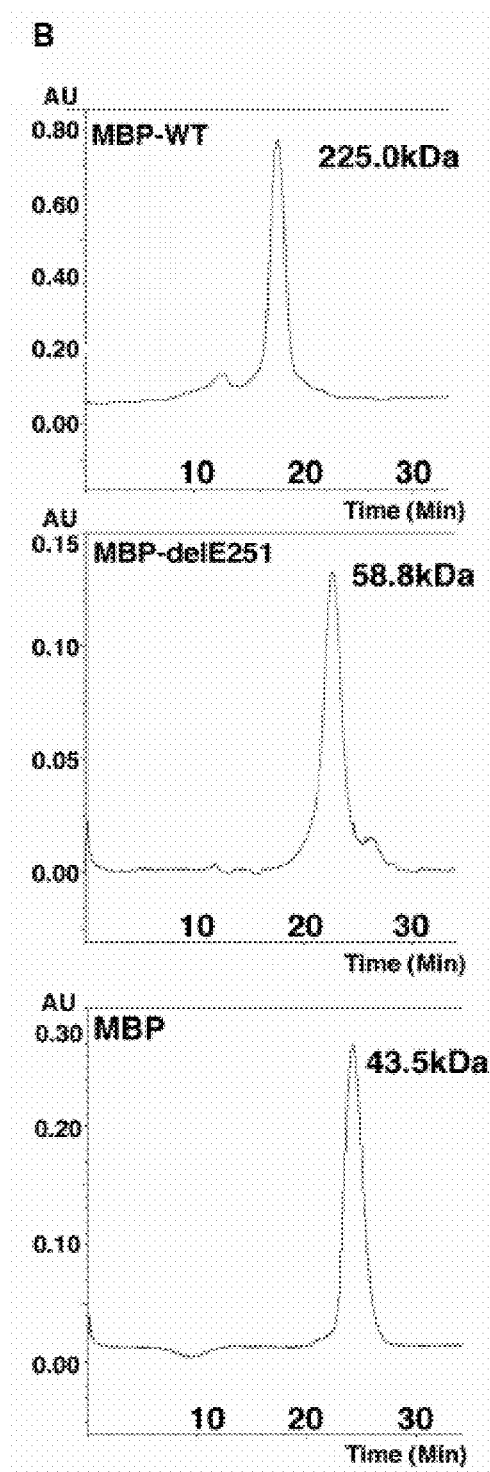

The critical N-terminal 196-264 amino acids of wild type FOXP3 containing the intact zinc finger and leucine zipper domains (Zinc-LeuZip), as well as the same fragment of the delE251 mutated FOXP3 were expressed in Escherichia coli (FIG. 3A). The Zinc-LeuZip fragments of wild type FOXP3 and delE251 FOXP3 were highly expressed and were purified as MBP fusion proteins. The MBP tag alone was also expressed and purified. The MBP fused Zinc-LeuZip fragment contains 497 amino acids with a predicted molecular weight of 54.9 kDa. The determination of protein molecular weights in solution was based on the elution volume from a Superdex 200 gel filtration column. Gel Filtration HMW and LMW Calibration Kits (Amersham Biosciences) were used for the calibration of Superdex 200 gel filtration column (Protein KW-803).

Although the purified wild type FOXP3 MBP-Zinc-LeuZip (MBP-WT) and FOXP3 delE251 MBP-Zinc-LeuZip (MBP-delE251) eluted as single peaks on gel filtration, the wild type MBP-Zinc-LeuZip eluted with an apparent molecular weight of 225.0 kDa, while the delE251 MBP-Zinc-LeuZip eluted as a single peak at 58.8 kDa (FIG. 3B). The peak protein fractions were concentrated and further examined by SDS-PAGE (FIG. 3C). Given the apparent molecular weight of both the wild type and delE251 proteins of approximately 50 kDa on SDS-PAGE, chromatography results indicate that the purified MBP-WT forms a homo-tetramer in solution (FIG. 3B, upper panel), while MBP-delE251 is monomeric (FIG. 3B, middle panel). A TEV protease cleavable MBP-tag expression vector was developed, and purified wild type FOXP3 Zinc-LeuZip alone as a tetramer. In summary, the zinc finger and leucine zipper domains of FOXP3 were found to be sufficient to mediate homotetramerization, and that one amino acid deletion (E251) within the leucine zipper domain, as found in human XLAAD/IPEX patients, disrupts this homotetramerization. FOXP3 and fragments derived from it can be found in dimeric or tetrameric associations.

Example 4

FOXP3 with FOXP1 Hetero-Oligomerization

Figure 4:
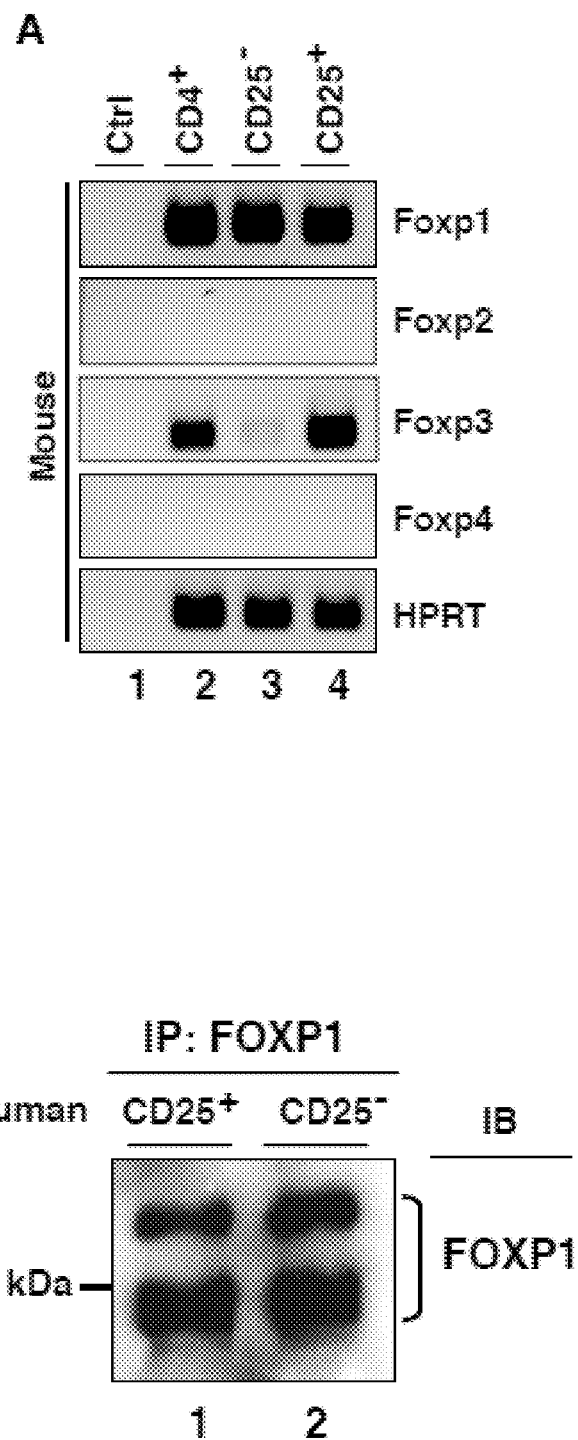
FIG. 4A is an image depicting the detection of the levels of Foxp1, Foxp2, FOXP3 and Foxp4 transcription in the cell population of murine $CD4^+CD25^+$ and $CD4^+CD25^-$ T cells using a radioprobe.
FIG. 4B is an image of an immunoblot detecting FOXP1 in human T cells. The human $CD4^+CD25^+$ and $CD4^+CD25^-$ T cells were lysed and subject to immunoprecipitation by an anti-FOXP1 antibody, resolved by gel electrophoresis and subject to immunoblotting with an anti-FOXP1 antibody.
FIG. 4C is an image of an immunoblot detecting FOXP3 and FOXP1 in HEK 293T cells. HEK 293T cells were co-transfected with expression plasmids for FLAG-FOXP1, myc-FOXP3a, myc-delE251 FOXP3a, or myc-delK250 FOXP3a as indicated. Cell lysates were immunoprecipitated with anti-FLAG, then immunoblotted with anti-myc 4E10 or anti-FLAG.
FIG. 4D is an image of an immunoblot detecting FOXP3 association with FOXP1 in human $CD4^+CD25^+$ T cells.
FIG. 4E is an image of an immunoblot detecting an impaired endogenous FOXP3-FOXP1 association in XLAAD/IPEX patient T cells.
FIG. 4F is an image of fluorescence microscopy of $CD4^+CD25^+$ T cells. Human $CD4^+CD25^+$ T cells were stimulated for 2 hrs with PMA/ionomycin, fixed, permeabilized and stained with either hFOXY anti-FOXP3 (red fluorescence) in conjunction with Rabbit anti-FOXP1 (green fluorescence) (left panel), or PCH101 rat anti-FOXP3 (green fluorescence) plus Rabbit anti-FOXP1 (red fluorescence) (right panel).
FIG. 4G is an image depicting the endogenous knockdown of FOXP1 in FOXP3 expressing Jurkat T cells relieved FOXP3 mediated repression on IL-2 production. The result is the average±standard error of mean of three independent experiments.
Figure 4:
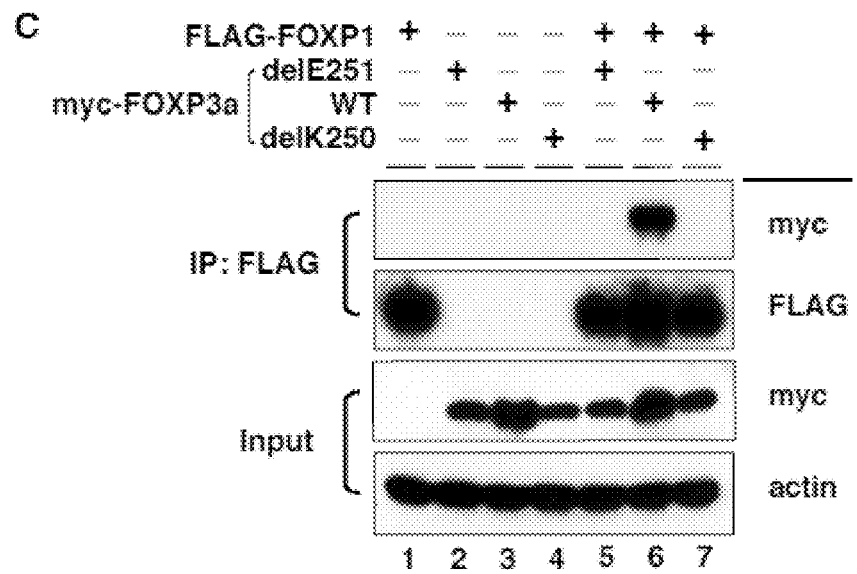
Figure 4:
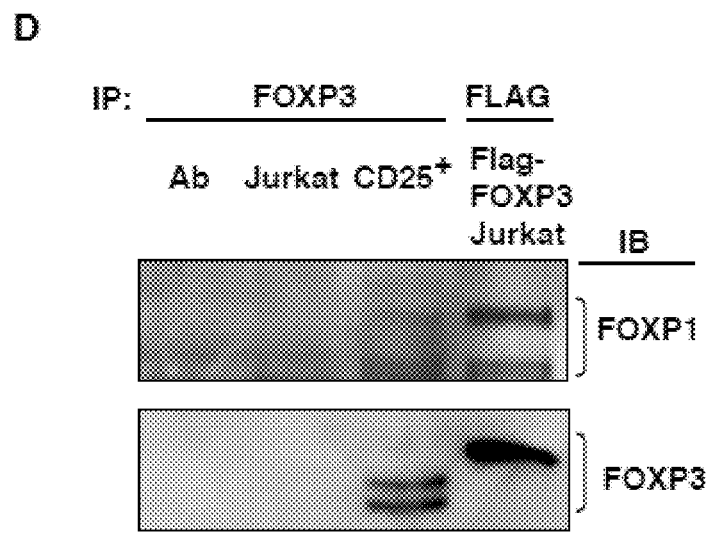
Figure 4:
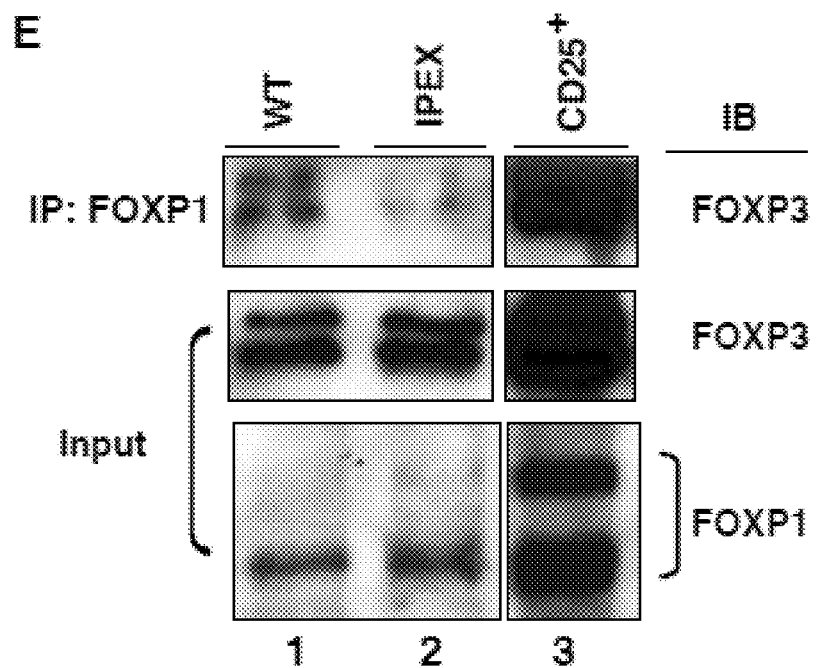
Figure 4:
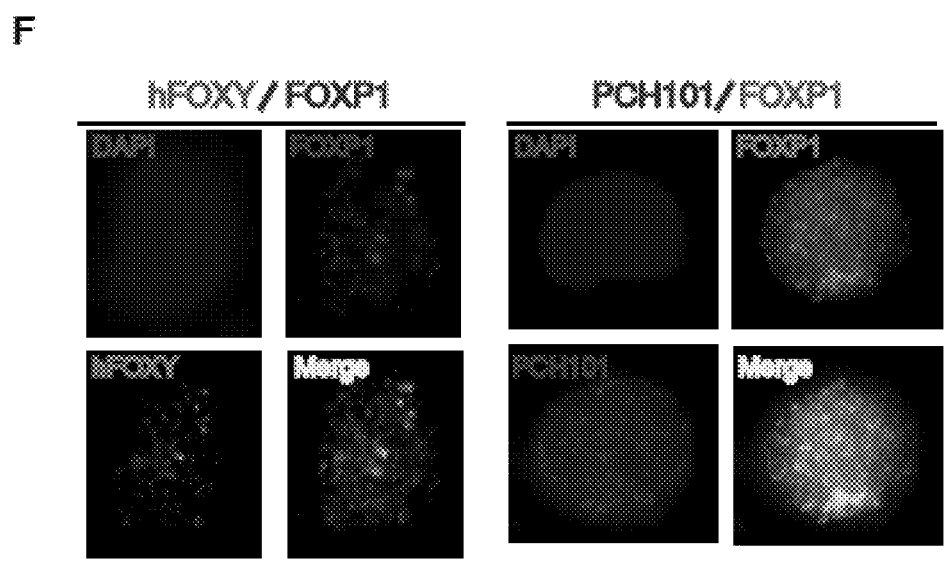

While FOXP1 was expressed equally in both $CD4^+CD25^+$ and $CD4^+CD25^-$ T cells, FOXP3 was expressed mainly in $CD4^+CD25^+$ T cells, and both FOXP2 and FOXP4 were undetectable in these primary murine $CD4^+$ T cells (FIG. 4A). To evaluate endogenous FOXP1 protein level in human $CD4^+$ T cells, nuclear extracts from in vitro expanded human $CD4^+$ $CD25^+$ T cells or $CD4^+CD25^-$ T cells were immunoprecipitated with anti-FOXP1 monoclonal antibody JC12, then immunoblotted with the same antibody. Endogenous FOXP1 was abundantly expressed as multiple isoforms in both human $CD4^+CD25^+$ T cells and $CD4^+CD25^-$ T cells (FIG. 4B). Ectopically expressed wild type human FOXP3, but neither K250 nor E251 deletion mutants, hetero-associated with the subfamily member FOXP1 (FIG. 4C). Endogenous FOXP1 co-precipitated with endogenous FOXP3 in human $CD4^+CD25^+$ T cells as well as in FOXP3 transfected Jurkat E6.1 T cells (FIG. 4D). Furthermore, endogenous FOXP3 was observed to colocalize with FOXP1 at many sites within the nucleus of human $CD4^+CD25^+$ T cells (FIG. 4F).

Figure 4G:
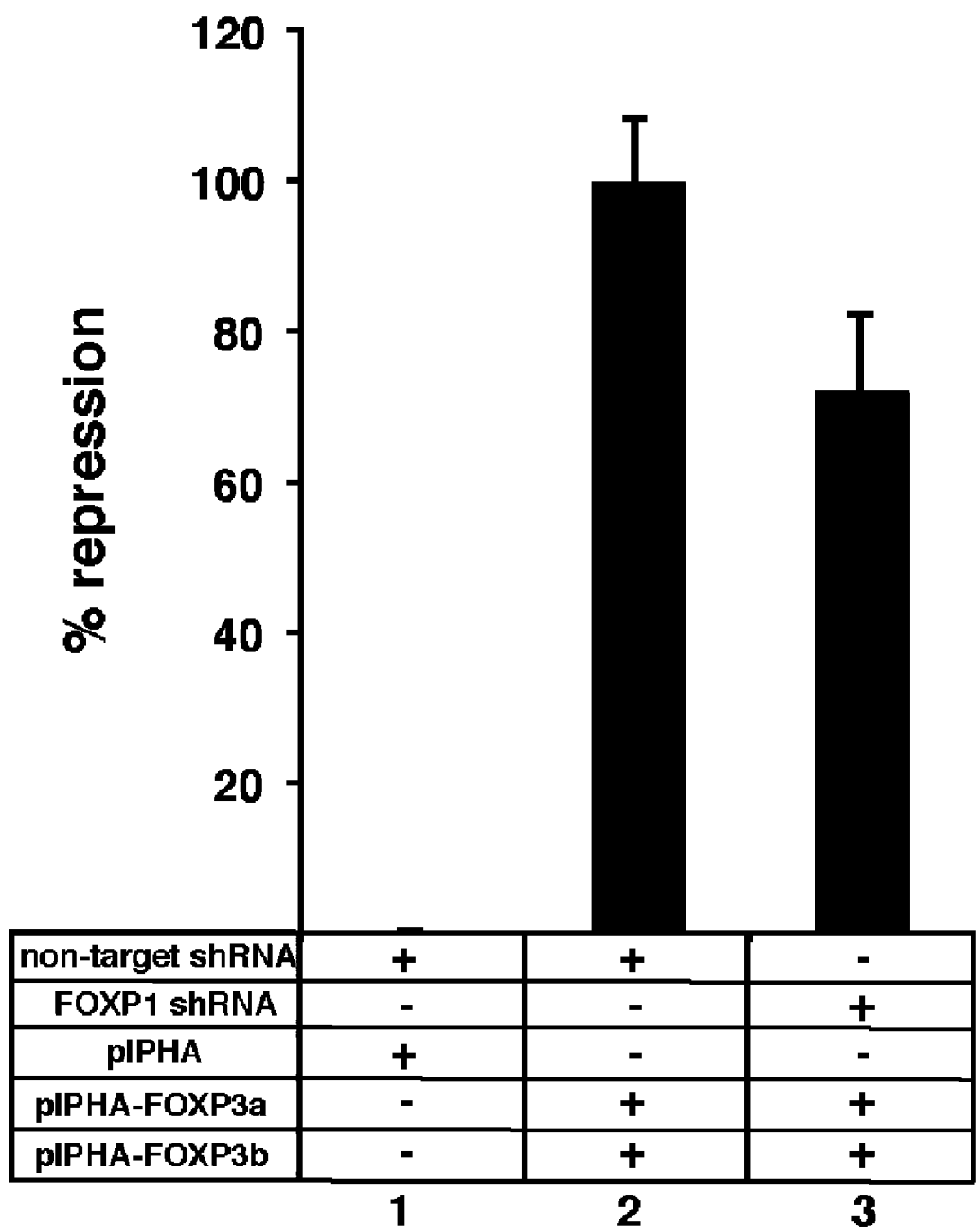

Nuclear extracts from a human T cell line derived from XLAAD/IPEX patient PBLs expressing delE251 mutant FOXP3 or from a normal control human T cell line expressing wild type FOXP3 were immunoprecipitated with the JC12 FOXP1 monoclonal antibody, then immunoblotted with anti-FOXP3 monoclonal antibody 221D (FIG. 4F). These endogenous co-immunoprecipitation experiments revealed that wild type FOXP3 hetero-associated with FOXP1, but FOXP3 from XLAAD/IPEX patient T cells containing the E251 deletion was impaired in its ability to hetero-associate with FOXP1 (FIG. 4F). Moreover, knockdown of endogenous FOXP1 expression by lentiviral vector mediated shRNA specific to FOXP1 TRCN0000015664 (sh64) in FOXP3 expressing Jurkat T cells partially relieved FOXP3 mediated repression of IL-2 production (FIG. 4G). These findings suggest that FOXP1-FOXP3 hetero-association may play an important, but presently undefined role in human regulatory T cells.

Example 5

FOXP3 Oligomerization and IL-2 Promoter Binding

Interleukin-2 is a critical cytokine for the regulation of peripheral T cell tolerance and regulatory T cell function. CD4 CD25+ regulatory T cells suppress polyclonal T cell activation in vitro by inhibiting interleukin-2 production. Ectopic expression of FOXP3 was sufficient to divert naïve T cells toward a regulatory T cell phenotype capable of suppressing proliferation of other T cells, through inhibition of IL-2 production. Putative forkhead binding sites have been identified adjacent to the NFAT sites in the human IL-2 promoter. Moreover, under some circumstances, FOXP3 physically associates with NFAT and NF-κB transcription factors and has been found to block their ability to induce IL-2.

Figure 5:
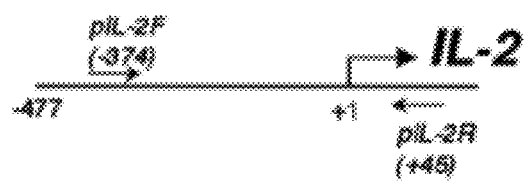
FIG. 5A is an image of an immunoblot wherein nuclear extracts from primary normal and XLAAD/IPEX patient (delE251) T cell lines were immunoblotted with monoclonal antibody 221D. The β-actin protein level was determined to show equivalence of nuclear extracts.
FIG. 5B is an image of an immunoblot wherein wild type and XLAAD/IPEX nuclear extracts were immunoprecipitated by anti-FOXP3 monoclonal antibody hFOXY (eBioscience), resolved by gel electrophoresis and subject to immunoblotting with anti-FOXP3 monoclonal antibody 221D.
FIG. 5C is a schematic representation of the primers used for detection of human IL-2 promoter region.
FIG. 5D is an image of an agarose gel of ChIP PCR results showing that wild type FOXP3 from primary normal T cells, but not the mutant FOXP3 from delE251 T cells, associates with IL-2 promoter. DNA from 1% of input for the immunoprecipitation was used as a positive control. Normal mouse IgG (IgG) and anti-acetyl-histone 4 antibody were used as the positive control for immunoprecipitation of transcriptionally active chromatin. Mouse anti-human FOXP3 monoclonal antibody hFOXY was used for immunoprecipitation of FOXP3.
Figure 5:
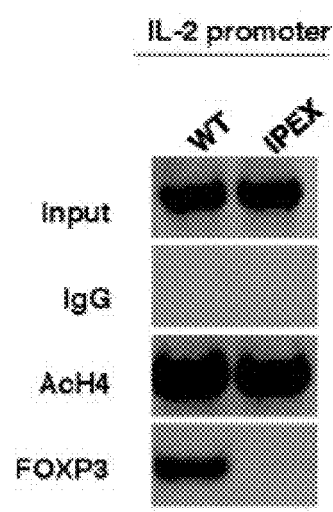

A primary human T cell line from an XLAAD/IPEX patient expressing FOXP3 with the E251 deletion (delE251) and a normal primary human T cell line expressing wild type FOXP3 were shown to express FOXP3 equivalently (FIG. 5A). After determining that monoclonal antibody hFOXY could immunoprecipitate wild type FOXP3 and delE251 FOXP3 equally (FIG. 5B), a pair of primers were used to detect the recruitment of endogenous FOXP3 to the human IL-2 promoter in vivo by chromatin immunoprecipitation (FIG. 5C). Endogenous wild type FOXP3 from normal human T cells associated with the human IL-2 promoter, whereas FOXP3 from human XLAAD/IPEX patient T cells containing the E251 deletion did not associate with the human IL-2 promoter (FIG. 5D). Although FOXP3 is part of a supramolecular complex, it is the oligomerized structure of wild type FOXP3 that occurs via the zinc finger and leucine zipper domains that is required for the efficient recruitment of FOXP3 to the IL-2 promoter in vivo.

To examine the direct binding of FOXP3 to the IL-2 promoter in vitro, electrophoretic mobility shift assays (EMSA) were performed using a probe from the IL-2 promoter that contains a consensus NFAT binding site adjacent to a potential forkhead binding site (the NFAT probe). Purified FOXP3-c106-431 (FIG. 6C lane 6) and nuclear extracts from wild type FOXP3 expressing Jurkat cells (FIG. 6C lane 3), but not the vector control extracts (FIG. 6C lane 2), bound to the probe. This binding was specific since it was competed with cold probe or with the 400 bp human IL-2 promoter region used in the chromatin immunoprecipitation assay (FIG. 5C). Binding of the NFAT probe was reduced when the FOXP3 E251 deletion mutant expressing nuclear extracts was used (FIG. 6C lane 4), indicating that deletion of a single amino acid within the leucine zipper domain, as in XLAAD/IPEX patients, impairs FOXP3 binding to the Forkhead binding site adjacent to the NFAT site in the IL-2 promoter. FOXP3 levels were equivalent in wild type and E251 deletion mutant transfectants.

Example 6

Reduced Repression of IL-2 Transcription by FOXP3 Mutant

IL-2 promoter activity was measured in Jurkat T cells ectopically expressing graded amounts of the wild type FOXP3 or the FOXP3 E251 deletion mutant and co-transfected with the full length IL-2-Luciferase reporter and control TK-Renilla luciferase vectors. Wild type FOXP3 repressed expression of the luciferase reporter driven by the IL-2 promoter in a dose dependent manner (FIG. 6D, lane 2, 3, 4). In contrast, the FOXP3 E251 mutant was less efficient, but not absolutely defective in repressing IL-2 transcription (FIG. 6D, lane 5, 6, 7). These data show the molecular basis for disease in human XLAAD/IPEX patients carrying the FOXP3 E251 or K250 mutation is a dysfunctional leucine zipper motif disrupting FOXP3 oligomerization and modifying its repressive function by preventing efficient interactions with sequence specific DNA.

Example 7

FOXP3 Domain for FOXP3 Activity

To further characterize the mechanism by which FOXP3 represses transcription, the interaction of FOXP3 with TIP60 was studied. A proline to serine change at position 177, which is within the proline rich motif, was created by site directed mutagenesis. HEK 293T cells were co-transfected with expression plasmids for FLAG-tagged TIP60, HA-tagged FOXP3a, or HA-tagged P177S mutant as indicated. (FIG. 7B). Forty-eight hours after transfection, cell lysates were immunoprecipitated with anti-HA mAb, then analyzed by Western blotting with anti-FLAG M2 mAb, and reprobed with anti-HA-HRP mAb. TIP60 and FOXP3 expression levels in cell lysates were analyzed by immunoblotting with FLAG M2 and HA-HRP respectively. The P177S mutant FOXP3 did not co-precipitate with TIP60 (FIG. 7B). Thus, the N-terminal 106-190 amino acids of FOXP3 are required for TIP60-FOXP3 and HDAC7-FOXP3 association (FIG. 7A).

Example 8

FOXP3 Oligomerization In Vivo

FOXP3 repressor ensemble complexes were immunoprecipitated from human breast tumor-derived SKBR3 cells transfected with FOXP3a or a mutant of FOXP3a that has an K>R mutation at residue 8 (FIG. 8). Nuclear extracts from 100 million either wild type HA-FOXP3a or K8R mutated HA-FOXP3a-K8R expressing SKBR3 cells were immunoprecipitated with either protein A/A-agarose or anti-HA-agarose beads, separated by SDS-PAGE, then stained with Silver staining reagent. Distinct bands were excised and analyzed with MS/Qstar sequencing.

Previous studies have shown than many proteins in lymphoid cells associate with FOXP3. These proteins include (1) the histone modification enzymatic complexes including subunits of the previously identified TIP60 complex TIP49a and TIP49b, the arginine methylase PRMT5; (2) the chromatin remodeling factors such as BRG1 and ISWI that regulate chromatin remodeling; (3) the molecular chaperones including GRP78 and Hsc70 which may regulate FOXP3 stability, oligomerization and binding to chromatin; (4) ch-TOG, a nuclear protein involved in spindle formation and centrosome assembly, whose role is unclear, and may mediate FOXP3's function via a novel mechanism; (5) RNA-binding protein 10 and several snRNP proteins including snRNP A1 and A0 A2/B1 which indicate that some FOXP3 species may regulate post-transcriptional maturation and/or RNA metabolism; and (6) Linker histone H1, which is a species that can incorporate into specific regions of the genome to regulate site-specific transcriptional repression.

The complex formation and alteration of the complex formation in response to extracellular stimuli were studied. First, the subunit components of the FOXP3 complex identified by MS/Qstar sequencing above were studied. Jurkat T cells were transfected with a FLAG-FOXP3 construct and stimulated with PMA (50 ng/mL) and Ionomycin (1 µM) stimulation (FIG. 9) for 72 hours. Then, nuclear extracts were size-fractionated by gel filtration followed by fraction concentration, SDS-PAGE and immunoblotting with FLAG M2, FOXP1, NFATc2, TIP60, HDAC7, MBD3 or BRG1 antibody respectively.

Consistent with the co-fractionation pattern in human CD4$^+$CD25$^+$ Treg cells, ectopically expressed FOXP3 constitutes part of large molecular weight complexes. The previously identified FOXP3-associated transcriptional factors FOXP1 and NFATc2, and the transcriptional co-repressors TIP60 and HDAC7, were all co-fractionated with FOXP3 in the lower molecular weight complex (FIG. 9 lane 6, 7, 8), while the chromatin remodeling factors BRG-1 and MBD3 were co-fractionated with FOXP3 in the higher molecular weight complexes (FIG. 9 lane 3, 4, 5). TIP60 was observed as a lower MW form in the lower molecular weight FOXP3 complex (FIG. 9 lanes 6, 7, 8) while a higher MW form of TIP60 was detected in the higher molecular weight FOXP3 complex containing the chromatin remodeling factors (FIG. 9 lanes 4, 5). Post-translational modification could be responsible for that change in the apparent MW of TIP60.

Example 9

TGF-β Modulates FOXP3 Activity

Human CD4$^+$CD25$^+$ Treg cells were incubated in the presence or absence of Transforming Growth Factor-β ("TGF-β") and FOXP3 binding to the IL-2 promoter was determined by ChIP assays. 10 million FOXP3 transfected cells were either treated with TGF-β or left untreated. The cells were then used for a ChIP analysis per the manufacturer's instructions and using mIgG, anti-AcH3, and anti-HA antibodies. Genomic DNA fragments were purified, then amplified with hIL-2 promoter specific primers by PCR using Platinum Taq DNA polymerase for 30 amplification cycles. 10 µl of amplified material was separated in 1.2% agarose gel, stained with ethidium bromide, and photographed under UV light (FIG. 10A).

These ChIP studies identified the occupancy of FOXP3 on the proximal region of the IL-2 promoter, which is regulated by extracellular stimuli such as TGF-β. To define the chromatin regions that are occupied by FOXP3, whether the binding of FOXP3 to chromatin is sensitive to Micrococcal nuclease (MNase) treatment was examined. MNase treatment freed FOXP3 from the chromatin-bound fraction; whereas, in the absence of MNase, only negligible amounts of FOXP3 were released from the chromatin.

The effect of TGF-β on the acetylation of FOXP3 was examined. Serum-starved human HA-FOXP3a/3b transfected Jurkat T cells were stimulated with or without 1 ng TGF-β per million cells for indicated time periods. Equal amounts of proteins from chromatin rich fractions were separated by SDS-PAGE, transferred to nitrocellulose, and immunoblotted with anti-acetyl lys specific antibody (Ac-K-103, Santa Cruz) followed by reprobing with anti-HA-HRP conjugated antibody (FIG. 9B). High levels of chromatin-bound acetylated FOXP3 were apparent between 2 and 4 hours after exposure to TGF-β (FIG. 10B).

What is claimed:

1. A method of identifying an immune response modulator, the method comprising:
   a) isolating
      i. a FOXP3 protein, or a fragment thereof having a Zinc-LeuZip domain, or a polynucleotide encoding said FOXP3 protein, or a fragment thereof having a Zinc-LeuZip domain;
      ii. HDAC7 protein or TIP60 protein, or a polynucleotide encoding said HDAC7 protein or TIP60 protein; and
      iii. a nucleic acid comprising an IL-2 promoter operably linked to a coding region;
   b) combining the isolated substances from step a;
   c) measuring transcription of the IL-2-linked coding region; and
   d) comparing the level of transcription of the IL-2-linked coding region that occurs in the presence of a chemical candidate to the level of transcription of the coding region that occurs in the absence of the chemical candidate,
   whereby the difference in level of transcription indicates that the chemical candidate is an immune response modulator.

* * * * *